(12) United States Patent
Holtcamp et al.

(10) Patent No.: US 9,321,854 B2
(45) Date of Patent: Apr. 26, 2016

(54) ALUMINUM ALKYL WITH C5 CYCLIC AND PENDENT OLEFIN POLYMERIZATION CATALYST

(71) Applicant: ExxonMobil Chemical Patents Inc., Baytown, TX (US)

(72) Inventors: Matthew W. Holtcamp, Huffman, TX (US); Gregory S. Day, Pasadena, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/520,605

(22) Filed: Oct. 22, 2014

(65) Prior Publication Data

US 2015/0119540 A1    Apr. 30, 2015

Related U.S. Application Data

(60) Provisional application No. 61/896,965, filed on Oct. 29, 2013.

(51) Int. Cl.

| C07F 5/06 | (2006.01) |
|---|---|
| C08F 8/00 | (2006.01) |
| C08F 8/44 | (2006.01) |
| C08F 4/602 | (2006.01) |
| C08F 4/02 | (2006.01) |

(52) U.S. Cl.
CPC . *C08F 4/602* (2013.01); *C07F 5/06* (2013.01); *C07F 5/061* (2013.01); *C07F 5/063* (2013.01); *C08F 4/02* (2013.01)

(58) Field of Classification Search
CPC .............. C08F 8/00; C08F 8/44; C07F 5/061; C07F 5/063
See application file for complete search history.

(56) References Cited

U.S. PATENT DOCUMENTS

| 5,308,811 | A | 5/1994 | Suga et al. |
|---|---|---|---|
| 5,928,982 | A | 7/1999 | Suga et al. |
| 5,973,084 | A | 10/1999 | Suga et al. |
| 6,040,261 | A | 3/2000 | Hlatky |
| 6,048,817 | A | 4/2000 | Sagae et al. |
| 6,147,173 | A | 11/2000 | Holtcamp |
| 6,211,105 | B1 | 4/2001 | Holtcamp |
| 6,239,062 | B1 | 5/2001 | Cribbs |
| 6,353,063 | B1 | 3/2002 | Shimizu et al. |
| 6,376,416 | B1 | 4/2002 | Hirakawa et al. |
| 6,376,629 | B2 | 4/2002 | Nagy et al. |
| 6,395,668 | B1 | 5/2002 | van Baar et al. |
| 6,395,846 | B1 | 5/2002 | Sato et al. |
| 6,414,162 | B1 | 7/2002 | Nagy |
| 6,451,724 | B1 | 9/2002 | Nifant'ev et al. |
| 6,489,480 | B2 | 12/2002 | Rodriguez |
| 6,531,552 | B2 | 3/2003 | Nakano et al. |
| 2002/0038036 | A1 | 3/2002 | Resconi et al. |
| 2002/0111446 | A1 | 8/2002 | Mukerjee et al. |
| 2003/0027950 | A1 | 2/2003 | Uchino et al. |
| 2003/0104928 | A1 | 6/2003 | Holtcamp |
| 2003/0164215 | A1* | 9/2003 | Woodson et al. ............... 149/87 |
| 2013/0041122 | A1* | 2/2013 | Holtcamp et al. ............ 526/171 |

FOREIGN PATENT DOCUMENTS

| EP | 0 511 665 A2 | 11/1992 |
|---|---|---|
| EP | 0 511 665 B1 | 7/1998 |
| EP | 1 160 261 | 12/2001 |
| JP | 05-025214 | 2/1993 |
| JP | 11-166011 | 6/1999 |
| JP | 11-166012 | 6/1999 |
| JP | 11-255816 | 9/1999 |
| JP | 2000-072813 | 3/2000 |
| JP | 2000-198812 | 7/2000 |
| JP | 2001-026613 | 1/2001 |
| JP | 2001-031720 | 2/2001 |
| JP | 2001-163908 | 6/2001 |
| JP | 2001-163909 | 6/2001 |
| JP | 2001-200010 | 7/2001 |
| JP | 2001-316414 | 11/2001 |
| JP | 2001-316415 | 11/2001 |
| JP | 2002-020415 | 1/2002 |
| JP | 2002-037812 | 2/2002 |
| JP | 2002-060411 | 2/2002 |
| JP | 2002-069116 | 3/2002 |
| JP | 2002-253486 | 9/2002 |
| KR | 10-2000-0069756 | 11/2000 |
| KR | 10-2001-0102158 | 11/2001 |
| KR | 10-2002-0034193 | 8/2002 |
| KR | 10-2012-0092977 | 8/2012 |
| WO | WO 00/11044 | 3/2000 |
| WO | WO 00/22010 | 4/2000 |
| WO | WO 01/23442 | 4/2001 |
| WO | WO 01/30864 | 5/2001 |
| WO | WO 01/42320 | 6/2001 |
| WO | WO 02/102811 | 12/2002 |
| WO | WO 03/064433 | 8/2003 |
| WO | WO 03/064435 | 8/2003 |

OTHER PUBLICATIONS

U.S. Appl. No. 61/907,471, Nov. 22, 2013, Holtcamp.
Kehr, et al., "($N$-Pyrrolyl)$B(C_6F_5)_2$: A New Organometallic Lewis Acid for the Generation of Group 4 Metallocene Cation Complexes," Chemistry—A European Journal, 2000, vol. 6, No. 2, pp. 258-266.
Kondakov et al., "*Zirconium-Catalyzed Enantioselective Methylalumination of Monosubstituted Alkenes,* " Journal of the American Chemical Society, vol. 117, No. 43, Nov. 1, 1995, pp. 10771-10772.
Lapoointe et al., "*New Family of Weakly Coordinating Anions,*" Journal of the American Chemical Society, vol. 122, Issue 39, pp. 9560-9561.

* cited by examiner

*Primary Examiner* — Caixia Lu

(57) ABSTRACT

This invention relates to organoaluminum compounds, to organoaluminum activator systems, preferably supported, to polymerization catalyst systems containing these activator systems and to polymerization processes utilizing the same. In particular, this invention relates to catalyst systems comprising an ion-exchange layered silicate, an organoaluminum compound, and a metallocene.

16 Claims, No Drawings

ALUMINUM ALKYL WITH C5 CYCLIC AND PENDENT OLEFIN POLYMERIZATION CATALYST

FIELD OF THE INVENTION

This invention claims priority to and the benefit of U.S. Ser. No. 61/896,965, filed Oct. 29, 2013.

The present invention relates to organoaluminum compounds, to organoaluminum activator systems, preferably supported, to polymerization catalyst systems containing these activator systems and to polymerization processes utilizing the same. In particular, this invention relates to catalyst systems comprising an ion-exchange layered silicate, an organoaluminum compound and a metallocene.

BACKGROUND OF THE INVENTION

Metallocene olefin polymerization catalyst systems typically use an activator (also called a co-catalyst) to generate the active catalytic species. In general, there are two catalyst activator families: partially hydrolyzed aluminum alkyl complexes and non-coordinating anions (NCA's). Some of the most commonly employed activators used today are the partially hydrolyzed aluminum alkyls, more specifically, alumoxanes, such as methylalumoxane (MAO). In general, metallocene olefin polymerization systems that utilize NCA-type activators are more active than their MAO counterparts, but are also quite costly and much more sensitive to poisons which present a problem in catalyst synthesis, handling, storage and reactor operation. Alternatively, MAO-based systems are more robust than their NCA-type counterparts, but they suffer from the high cost of MAO production, the fact that MAO is typically used in large excess (relative to the amount of metallocene) and the limited shelf life of MAO.

In order to enhance polymer morphology, metallocene polymerization catalysts operated in industrial slurry and gas phase processes are typically immobilized on a carrier or a support, such as alumina or silica. Metallocenes are supported to enhance the morphology of the forming polymeric particles such that they achieve a shape and density that improves reactor operability and ease of handling. However, the supported versions of metallocene polymerization catalysts tend to have lower activity as compared to their homogeneous counterparts. In general, metallocene and single-site catalysts are immobilized on silica supports.

Alternative supports for metallocene and single-site catalysts have been the subject of numerous ongoing research projects. In particular, metallocenes supported on clay or ion-exchanged layered compounds have generated interest. Olefin polymerization catalysts using clay, clay mineral or acid/salt-treated (or a combination of both) ion-exchange layered compounds, an organoaluminum compound and a metallocene as components have been reported (see EP 0 511,665A2; EP 0 511,665B1; and U.S. Pat. No. 5,308,811). Likewise, U.S. Pat. Nos. 5,928,982 and 5,973,084 report olefin polymerization catalysts containing an acid or salt-treated (or a combination of both) ion exchange layered silicate, containing less than 1% by weight water, an organoaluminum compound and a metallocene. Furthermore, WO 01/42320A1 discloses combinations of clay or clay derivatives as a catalyst support, an activator comprising any Group 1-12 metal or Group 13 metalloid, other than organoaluminum compound, and a Group 3-13 metal complex. Also, U.S. Pat. No. 6,531,552B2 and EP 1,160,261A1 report an olefin polymerization catalyst of an ion-exchange layered compound having particular acid strength and acid site densities. US 2003/0027950A1 reports an olefin polymerization catalyst utilizing ion-exchange layered silicates with a specific pore size distribution and having a carrier strength within a specific range.

Likewise, alternative activators for metallocenes and other single-site polymerization catalysts have been the subject of research efforts in recent years. For example, perfluorophenyl aluminum and borane complexes containing one anionic nitrogen-containing group may activate metallocenes. For example, R. E. Lapointe, G. R. Roof, K. A. Abboud, J. Klosin, J. Am. Chem. Soc. 2000, 122, pp. 9560-9561, and WO 01/23442A1 report the synthesis of $(C_6F_5)_3Al$ (imidazole) $[Al(C_6F_5)_3][HNR'R'']$. In addition, G. Kehr, R. Frohlich, B Wibbeling, G. Erker, Chem. Eur. J. 2000, 6, No.2, pp. 258-266 report the synthesis of $(N-Pyrrolyl)B(C_6F_5)_2$. Supported activators containing a Group 13 element and at least one halogenated, nitrogen-containing aromatic group ligand for polymerization catalysts have been reported (U.S. Pat. Nos. 6,147,173 and 6,211,105). J. Am. Chem. Soc, 1995, 117, 10771-10772 discloses the reaction of various monosubstituted alkenes containing hydrocarbon substituents as well as those containing heteroatom substituents with $Me_3Al$ and a catalytic amount of a chiral zirconocene derivative provides, after oxidation with oxygen, 2-methyl-1-alkanols in generally high yields. Other references of interest include: U.S. Ser. No. 61/907,471, filed Nov. 22, 2013; US 2003-104928; WO 2003/064433; U.S. Pat. No. 6,489,480; US 2002-038036; WO 2002/102811; U.S. Pat. Nos. 6,414,162; 6,040,261; 6,239,062; 6,376,629; 6,451,724; JP 2002-069116A; JP 2002-0253486A; US 2003-0027950A1; JP 2002-037812A; JP 2002-020415A; JP 2002-060411A; JP 2001-316415A; JP 2001-316414A; U.S. Pat. No. 6,531,552; JP 2001-200010A; JP 2001-163909A; JP 2001163908A; WO 2001-30864A1; JP 2001-026613A; JP 2001-031720A; JP 2000-198812A; WO 2000/22010A1; JP 2000072813A; WO 2000/11044A1; U.S. Pat. Nos. 6,353,063; 6,376,416; JP 11255816A(1999-09-21); JP 11166012A(1999-06-22); JP 11166011A(1999-06-22); U.S. Pat. No. 6,048,817; JP 05025214A(1993-02-02); WO 2003/064433A1; WO 2003/0644435A1; and US 2002/111446.

Given the high cost, low stability and reduced activity of MAO-based metallocene polymerization systems, there is a need in the art for new inexpensive, stable and supportable polymerization catalyst activator compounds.

SUMMARY OF THE INVENTION

This invention relates to supported activators comprising the product of the combination of an ion-exchange layered silicate, and an organoaluminum activator compound. This invention further relates to catalyst systems comprising metallocene catalyst compounds and such supported activators, as well as processes to polymerize unsaturated monomers using the catalyst systems comprising the supported activators.

The organoaluminum compounds described herein are the reaction product(s) of vinyl terminated cyclic olefins and trialkyl aluminums. The vinyl terminated cyclic olefin is the product of a cyclic olefin and an olefin via a ring opening cross metathesis reaction (ROCM), wherein the olefin is preferably an alpha-olefin. A ruthenium catalyst is used in the cross metathesis reaction. The vinyl terminated cyclic olefin and the aluminum alkyl are combined and heated to produce the organoaluminum compound(s), which is useful as an activator or a scavenger when utilized with metallocene catalysts to prepare polymers, such as polypropylene.

This invention also relates to a composition comprising the reaction product of: Al(R)$_3$ and a compound represented by the formula (I):

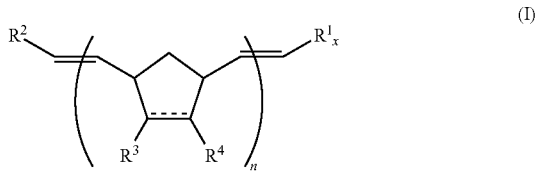

wherein the dotted line indicates an optional double bond; x is 0 or 1; the double bonds depicted as trans can each, independently, be cis or trans; $R^1$ and $R^2$ can be the same or different and each is a hydrogen atom or hydrocarbyl group having from one to twenty carbon atoms; $R^3$ and $R^4$ can be the same or different and each is a hydrogen atom or a hydrocarbyl group having from one to forty carbon atoms or $R^3$ and $R^4$ may be joined together to form a five-membered or six-membered ring, the ring having one or two optional double bonds, provided that at least one of $R^1$ or $R^2$ is a hydrogen atom such that a vinyl end group is present; n is an integer from 1 to 100; and wherein each R, independently, is a hydrogen atom or a $C_1$ to a $C_{30}$ branched or unbranched alkyl group.

This invention also relates to compositions represented by the formula:

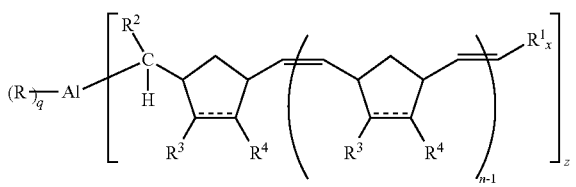

wherein the dotted line indicates an optional double bond; x is 0 or 1; the double bonds depicted as trans can each, independently, be cis or trans; $R^1$ and $R^2$ can be the same or different and each is a hydrogen atom or hydrocarbyl group having from one to twenty carbon atoms; $R^3$ and $R^4$ can be the same or different and each is a hydrogen atom or a hydrocarbyl group having from one to forty carbon atoms or $R^3$ and $R^4$ may be joined together to form a five-membered or six-membered ring, the ring having one or two optional double bonds; n is an integer from 1 to 100; wherein each R, independently, is a hydrogen atom or a $C_1$ to a $C_{30}$ branched or unbranched alkyl group; and z+q=3. This invention also relates to catalyst systems comprising a metallocene catalyst; and the aforementioned composition.

DEFINITIONS

For the purposes of this patent specification and the claims thereto, the term "activator" is used interchangeably with the term "co-catalyst", the term "catalyst" refers to a metal compound that when combined with an activator polymerizes olefins, and the term "catalyst system" refers to the combination of a catalyst and an activator with or without a support. The terms "support" or "carrier", for purposes of this patent specification, are used interchangeably and are any ion-exchange layered silicates.

As used herein, the new notation for the Periodic Table Groups is used as described in *Chemical and Engineering News*, 63(5), 27 (1985).

The term "substituted" means that a hydrogen group has been replaced with a hydrocarbyl group, a heteroatom, or a heteroatom containing group. For example, methyl cyclopentadiene (Cp) is a Cp group substituted with a methyl group and ethyl alcohol is an ethyl group substituted with an —OH group.

An "olefin," alternatively referred to as "alkene," is a linear, branched, or cyclic compound of carbon and hydrogen having at least one double bond. For purposes of this specification and the claims appended thereto, when a polymer or copolymer is referred to as comprising an olefin, including, but not limited to, ethylene and or propylene, the olefin present in such polymer or copolymer is the polymerized form of the olefin. For example, when a copolymer is said to have an "ethylene" content of 35 wt % to 55 wt %, it is understood that the mer unit in the copolymer is derived from ethylene in the polymerization reaction and said derived units are present at 35 wt % to 55 wt %, based upon the weight of the copolymer. A "polymer" has two or more of the same or different mer units. A "homopolymer" is a polymer having mer units that are the same. A "copolymer" is a polymer having two or more mer units that are different from each other. An ethylene polymer is a polymer having at least 50 mol % of ethylene, a propylene polymer is a polymer having at least 50 mol % of propylene, and so on.

Room temperature is defined as 25° C. unless otherwise specified.

Unless otherwise stated, Mn, Mw and Mz are determined using the following Gel Permeation Chromatography (GPC) method using a High Temperature Size Exclusion Chromatograph (SEC, either from Waters Corporation or Polymer Laboratories), equipped with a differential refractive index detector (DRI). Molecular weight distribution (MWD) is Mw (GPC)/Mn (GPC). Experimental details, are described in: T. Sun, P. Brant, R. R. Chance, and W. W. Graessley, *Macromolecules*, Volume 34, Number 19, pp. 6812-6820, (2001) and references therein. Three Polymer Laboratories PLgel 10 mm Mixed-B columns are used. The nominal flow rate is 0.5 cm$^3$/min and the nominal injection volume is 300 μL. The various transfer lines, columns and differential refractometer (the DRI detector) are contained in an oven maintained at 135° C. Solvent for the SEC experiment is prepared by dissolving 6 grams of butylated hydroxy toluene as an antioxidant in 4 liters of Aldrich reagent grade 1,2,4 trichlorobenzene (TCB). The TCB mixture is then filtered through a 0.7 μm glass pre-filter and subsequently through a 0.1 μm Teflon filter. The TCB is then degassed with an online degasser before entering the SEC. Polymer solutions are prepared by placing dry polymer in a glass container, adding the desired amount of TCB, then heating the mixture at 160° C. with continuous agitation for about 2 hours. All quantities are measured gravimetrically. The TCB densities used to express the polymer concentration in mass/volume units are 1.463 g/mL at room temperature and 1.324 g/mL at 135° C. The injection concentration is from 1.0 to 2.0 mg/mL, with lower concentrations being used for higher molecular weight samples. Prior to running each sample the DRI detector and the injector are purged. Flow rate in the apparatus is then increased to 0.5 mL/minute, and the DRI is allowed to stabilize for 8 to 9 hours before injecting the first sample. The concentration, c, at each point in the chromatogram is calculated from the baseline-subtracted DRI signal, $I_{DRI}$, using the following equation:

$$c = K_{DRI} I_{DRI}/(dn/dc)$$

where $K_{DRI}$ is a constant determined by calibrating the DRI, and (dn/dc) is the refractive index increment for the system.

The refractive index, n=1.500 for TCB at 135° C. and λ=690 nm. For purposes of this invention and the claims thereto, (dn/dc)=0.104 for propylene polymers and ethylene polymers, and 0.1 otherwise. Units of parameters used throughout this description of the SEC method are: concentration is expressed in g/cm³, molecular weight is expressed in g/mol, and intrinsic viscosity is expressed in dL/g.

The following abbreviations may be used herein: Me is methyl, Et is ethyl, Pr is propyl, cPR is cyclopropyl, nPr is n-propyl, iPr is isopropyl, Bu is butyl, nBu is normal butyl, iBu is isobutyl, sBu is sec-butyl, tBu is tert-butyl, Oct is octyl, Ph is phenyl, Bz is benzyl, MAO is methylalumoxane, Ind is indenyl, Cp is cyclopentadienyl, Flu is fluorenyl, RT is room temperature (23° C., unless otherwise indicated).

DETAILED DESCRIPTION

This invention relates to supported activators comprising the product of the combination of an ion-exchange layered silicate, an organoaluminum compound and a metallocene catalyst.

In another embodiment, an organoaluminum compound is described as well as its preparation.

In still another embodiment, an organoaluminum compound and a metallocene catalyst are combined to provide a catalyst system. The organoaluminum compound/metallocene catalyst system can, with or without being supported on a solid support such as a silicate, be used to polymerize olefins, in particular, alpha-olefins such as propylene.

Vinyl Terminated Cyclic Olefins

The vinyl terminated cyclic olefins described herein include those prepared by a ring opening cross metathesis reaction between a cyclic olefin and an olefin with a ruthenium catalyst. Vinyl terminated cyclic olefins and their preparation are described in U.S. Ser. No. 13/209,242, filed Aug. 12, 2011, published as US Publication No. 20130041122, having a publication date of Feb. 14, 2013, the contents of which are incorporated herein in their entirety for all purposes. Details are provided below for the current embodiments described herein.

Cyclic Olefins

The cyclic olefin may be a single cyclic olefin, or a combination of cyclic olefins, that is a mixture of two or more different cyclic olefins. The cyclic olefins may be strained or unstrained, monocyclic, or polycyclic; and may optionally include heteroatoms and/or one or more functional groups. Suitable cyclic olefins include, but are not limited to, norbornene, norbornadiene, dicyclopentadiene, cyclopentene, cycloheptene, cyclooctene, cyclooctadiene, cyclododecene, 7-oxanorbornene, 7-oxanorbornadiene, and substituted derivatives therefrom. Illustrative examples of suitable substituents include, but are not limited to, hydroxyl, thiol, ketone, aldehyde, ester, ether, amine, imine, amide, nitro, carboxylic acid, disulfide, carbonate, isocyanate, carbodiimide, carboalkoxy, and halogen. Preferred cyclic olefins include cyclooctene, 1,5-cyclooctadiene, 1-hydroxy-4-cyclooctene, 1-acetoxy-4-cyclooctene, 5-methylcyclopentene, cyclopentene, dicyclopentadiene, norbornene, norbornadiene, and their respective homologs and derivatives, preferably norbornene, norbornadiene, and dicyclopentadiene.

In a preferred embodiment, the cyclic olefin is a strained olefin. Alternately, the cyclic olefin is multicyclic. For clarification, dicyclopentadiene, norbornene, norbornadiene, ethylidene norbornene, and vinyl norbornene are multicyclic.

In a preferred embodiment, the cyclic olefin is a $C_5$ based cyclic olefin. A $C_5$ based cyclic olefin is an olefin (preferably, a $C_5$ to $C_{20}$ olefin) derived from substituted or unsubstituted cyclopentadiene such as dicyclopentadiene, norbornene, norbornadiene, ethylidene norbornene, vinyl norbornene, and the like.

Linear Mono-Olefins

Any linear mono-olefin may be used for the metathesis reaction described herein. For example, an alpha olefin may be used. For the purposes of this invention and the claims thereto, the term "alpha olefin" refers to an olefin where the carbon-carbon double bond occurs between the alpha and beta carbons of the chain. Alpha olefins may be represented by the formula: $H_2C=CH-R^*$, wherein each $R^*$ is independently, hydrogen or a $C_1$ to $C_{30}$ hydrocarbyl; preferably, a $C_2$ to $C_{20}$ hydrocarbyl; preferably, a $C_3$ to $C_{12}$ hydrocarbyl; preferably, methyl, ethyl, propyl, butyl, pentyl, heptyl, octyl, nonyl, decyl, undecyl, dodecyl, and substituted analogs thereof. For example, 1-pentene, 1-hexene, 1-heptene, and 1-decene are alpha olefins that are particularly useful in embodiments herein.

In other embodiments, internal olefins may be used. For the purposes of this invention and the claims thereto, the term "internal olefin" means a double bond that is not a vinyl, vinylene, or vinylidene unsaturation, preferably the term "internal olefin" refers to an olefin where the double bond does not occur between the alpha and beta carbons of the chain. Internal olefins may be represented by the formula: $R^*HC=CH-R^*$, wherein each $R^*$ is independently, a $C_1$ to $C_{30}$ hydrocarbyl; preferably, a $C_2$ to $C_{20}$ hydrocarbyl; preferably, a $C_2$ to $C_{12}$ hydrocarbyl; preferably, methyl, ethyl, propyl, butyl, pentyl, hexyl, and substituted analogs thereof. For example, hex-2-ene, hept-3-ene, dec-5-ene are particularly useful in embodiments herein.

The linear mono-olefin may also be substituted at any position along the carbon chain with one or more substituents. In some embodiments, the one or more substituents are essentially inert with respect to the metathesis process. Suitable substituents include, without limitation, alkyl, preferably, $C_{1-6}$ alkyl; cycloalkyl, preferably, $C_{3-6}$ cycloalkyl; as well as hydroxy, ether, keto, aldehyde, and halogen functionalities.

Preferred linear mono-olefins include, ethylene, propylene, butene, pentene, hexene, octene, nonene, decene, undecene, dodecene, and the isomers thereof (particularly the isomers where the double bond is in the alpha position and isomers where the double bond is not in the alpha position).

Particularly preferred linear mono-olefins include dec-5-ene, 1-pentene, 1-hexene, 1-decene, and 1-octene.

Isomers of any of the linear mono-olefins are useful herein. In some embodiments, cis and/or trans isomers may be used.

Suitable cyclic vinyl terminated olefins useful in the preparation of the organoaluminum compounds disclosed herein include those described in U.S. Ser. No. 13/209,242, filed Aug. 12, 2011 and published as US Publication No. 2013-0041122, having a publication date of Feb. 14, 2013, the contents of which are incorporated herein in their entirety for all purposes.

For example, vinyl terminated cyclic olefins include those compounds represented by the formula (I):

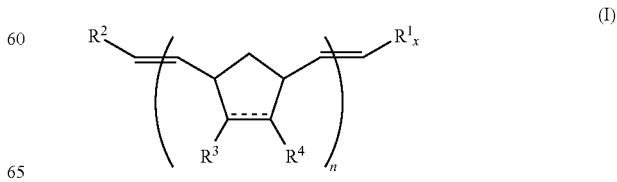

where the dotted line indicates an optional double bond;

x is 0 or 1;

the double bonds depicted as trans can each, independently, be cis or trans;

$R^1$ and $R^2$ can be the same or different and each is a hydrogen atom or hydrocarbyl group having from one to twenty carbon atoms (preferably 1 to 12, preferably 1 to 6, preferably 5 carbon atoms);

$R^3$ and $R^4$ can be the same or different and each is a hydrogen atom or a hydrocarbyl group having from one to forty carbon atoms (preferably 1 to 20, preferably 1 to 12, preferably 2 to 6 carbon atoms) or $R^3$ and $R^4$ may be joined together to form a five-membered or six-membered ring, the ring having one or two optional double bonds, provided that at least one of $R^1$ or $R^2$ is a hydrogen atom such that a vinyl end group is present; and n is an integer from 1 to 100 (preferably 1 to 60, preferably 2 to 20, preferably 2 to 10, preferably 2 to 5, alternately 1, 2, 3, 4, 5, 6, 7, 8, 9, 10, 11, or 12).

In a preferred embodiment, all or part of the $C_5$ ring(s) in formula (I) are saturated. In another embodiment all or part of the $C_5$ ring(s) in formula (I) are unsaturated. In another embodiment, the pentane ring(s) in formula (I) are saturated.

In still another embodiment, $R^1$ and $R^2$ are hydrogen atoms.

In another embodiment, $R^1$ or $R^2$ is a hydrogen atom, $R^3$ and $R^4$, each independently, are H or can be a $C_{5-9}$ hydrocarbyl and n is an integer from 1 to 100 (preferably from 1 to 50, preferably from 2 to 20, preferably from 4 to 10).

In yet another embodiment, $R^1$ is a hydrogen atom, $R^2$ is a $C_5$ or a $C_9$ hydrocarbyl, $R^3$ and $R^4$, each independently, are H or a $C_{5-9}$ hydrocarbyl and n is an integer from 1 to 100 (preferably from 1 to 50, preferably from 2 to 20, preferably from 4 to 10).

In another preferred embodiment, one of $R^1$ or $R^2$ is a $C_9$ hydrocarbyl and the other is a hydrogen atom.

In another preferred embodiment, $R^1$ or $R^2$ is a $C_9$ hydrocarbyl, $R^3$ and $R^4$ are H and n is an integer from 1 to 100 (preferably from 1 to 50, preferably from 2 to 20, preferably from 4 to 10, alternately 1, 2, 3, 4, 5, 6, 7, 8, 9, 10, 11, 12, 13, 14, 15, 16, 17, 18, 19, or 20).

In another embodiment, $R^3$ and $R^4$ form a $C_5$ unsaturated cyclic group, such as cyclopentene. In another embodiment, $R^3$ and $R^4$ form a $C_5$ saturated cyclic group, such as cyclopentane. In another embodiment, $R^3$ and $R^4$ form cyclopentene and/or cyclopentane.

Alkyl Aluminum Compounds

Alkyl aluminum compounds are represented by the formula:

$$AlR_3 \qquad (II)$$

wherein each R is independently, a hydrogen atom or a substituted or unsubstituted alkyl group and/or a substituted or unsubstituted aryl group. Optionally, one or more R groups can be a hydrogen atom. In one aspect, one or more R groups are an alkyl group containing 1 to 30 carbon atoms, alternately 2 to 20 carbon atoms. In a preferred embodiment of the invention, one, two, or three R groups are not H. In another embodiment of the invention, one, two, or three R groups are not methyl. In a preferred embodiment of the invention, one, two, or three R groups are H. In a preferred embodiment of the invention, one, two, or three R groups are a $C_1$ to $C_{30}$ alkyl group, alternately a $C_2$ to $C_{20}$ alkyl group. Suitable R groups include methyl, ethyl, propyl, butyl, isobutyl, pentyl, hexyl, heptyl, octyl, nonyl, decyl, undecyl, docecyl, aryl, and all isomers thereof. Trialkylaluminum compounds and dialkylaluminum compounds are suitable examples. Useful trialkylaluminum compounds include trimethylaluminum, triethylaluminum, triisobutylaluminum, tri-n-octylaluminum; $AlH_3$, and the like.

Organoaluminum Compounds

Organoaluminum compound reaction products between an alkyl aluminum ($AlR_3$) and a vinyl terminated cyclic olefin are provided.

In one aspect, the organoaluminum reaction product can be described as the reaction product of a compound represented by the formula (I):

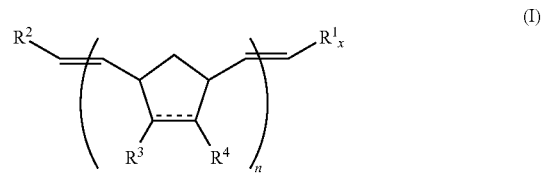

where the dotted line indicates an optional double bond;

x is 0 or 1;

the double bonds depicted as trans can each, independently, be cis or trans;

$R^1$ and $R^2$ can be the same or different and each is a hydrogen atom or hydrocarbyl group having from one to twenty carbon atoms (preferably 1 to 12, preferably 1 to 6, preferably 5 carbon atoms);

$R^3$ and $R^4$ can be the same or different and each is a hydrogen atom or a hydrocarbyl group having from one to forty carbon atoms (preferably 1 to 20, preferably 1 to 12, preferably 2 to 6 carbon atoms) or $R^3$ and $R^4$ may be joined together to form a five-membered or six-membered ring, the ring having one or two optional double bonds, provided that at least one of $R^1$ or $R^2$ is a hydrogen atom such that a vinyl end group is present; and n is an integer from 1 to 100 (preferably 1 to 60, preferably 1 to 20, preferably 2 to 10, preferably 2 to 5, alternately 1, 2, 3, 4, 5, 6, 7, 8, 9, 10, 11, 12, 13, 14, 15, 16, 17, 18, 19, or 20); and $AlR_3$ (compound II), wherein each R, independently, is a hydrogen atom or a $C_1$ to $C_{30}$ (alternately $C_2$ to $C_{20}$) branched or unbranched alkyl group or a substituted or unsubstituted aryl group.

In another aspect, the organoaluminum compound can be depicted by the formula:

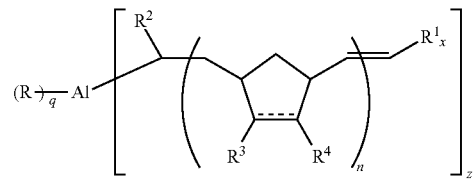

wherein $R^1$, $R^2$, $R^3$, $R^4$, each R if present, x, n, the dotted line and cis/trans relationships are as described above and wherein z+q=3. In one embodiment, z is 3 and q is 0. In another embodiment, z is 2 and q is 1. In another embodiment z is 1 and q is 2.

The organoaluminum compounds can be prepared by combining a trialkylaluminum, a dialkylaluminum hydride, a monoalkylaluminum dihydride or aluminum trihydride (aluminum hydride, $AlH_3$) with a vinyl terminated cyclic olefin and heating to a temperature that causes release of an alkylene byproduct. The use of solvent(s) is not required. However, non-polar solvents can be employed, such as, hexane, pentane, toluene, benzene, xylenes, or combinations thereof.

After the reaction is complete, solvent if present can be removed and the product can be used directly without further purification.

Bulky Ligand Metallocene Catalyst Compositions

A metallocene catalyst is defined as an organometallic compound with at least one π-bound cyclopentadienyl moiety (or substituted cyclopentadienyl moiety) and more frequently two π-bound cyclopentadienyl moieties or substituted cyclopentadienyl moieties. The supported or unsupported organoaluminum compounds described herein may be used to activate bulky ligand metallocene catalyst compositions. Generally, these catalyst compounds include half and full sandwich compounds having one or more bulky ligands bonded to at least one metal atom.

Typical bulky ligand metallocene compounds are described as containing one or more bulky ligand(s) and one or more leaving group(s) bonded to at least one metal atom. Suitable metallocene catalysts are described as follows and are also described in WO2005/068515, published Jul. 28, 2005, filed on Nov. 3, 2004 with an International Application No. PCT/US2004/036988, the contents of which are incorporated herein in their entirety for all purposes.

The bulky ligands may be open, acyclic, fused ring(s) or ring system(s), or a combination thereof. The ring(s) or ring system(s) of these bulky ligands are typically composed of atoms selected from Groups 13 to 16 atoms of the Periodic Table of the Elements. Preferably the atoms are selected from the group consisting of carbon, nitrogen, oxygen, silicon, sulfur, phosphorus, germanium, boron and aluminum or a combination thereof. Most preferably the ring(s) or ring system(s) are composed of carbon atoms such as, but not limited to, cyclopentadienyl ligands or cyclopentadienyl-type ligand structures. The bulky ligands may also be other similar functioning ligand structure such as a pentadiene, a cyclooctatetradienyl or an imide ligand. The metal atom is preferably selected from Group 3 through 15 and the lanthanide or actinide series of the Periodic Table of the Elements. Preferably the metal is a transition metal from Groups 4 through 12, more preferably Groups 4, 5 and 6, and most preferably the transition metal is from Group 4, especially Ti or Zr or Hf.

In one embodiment, the bulky ligand metallocene catalyst compounds, which may be utilized with the organoaluminum compound of the invention, may be represented by Formula IV:

(Formula IV)

where M is a metal atom from the Periodic Table of the Elements and may be a Group 3 to 12 metal or from the lanthanide or actinide series of the Periodic Table of the Elements, preferably M is a Group 4, 5 or 6 transition metal, more preferably M is zirconium, hafnium or titanium. The bulky ligands, $L^A$ and $L^B$, are open, acyclic or fused ring(s) or ring system(s) and are any ancillary ligand system, including unsubstituted or substituted cyclopentadienyl ligands or cyclopentadienyl-type ligands. Non-limiting examples of bulky ligands include cyclopentadienyl ligands, cyclopentaphenanthreneyl ligands, indenyl ligands, benzindenyl ligands, fluorenyl ligands, octahydrofluorenyl ligands, cyclooctatetraenyl ligands, cyclopentacyclododecene ligands, azenyl ligands, azulene ligands, pentalene ligands, phosphoyl ligands, phosphinimine ligands (WO 99/40125), pyrrolyl ligands, pyrazolyl ligands, carbazolyl ligands, borabenzene ligands and the like, including hydrogenated versions thereof, for example tetrahydroindenyl ligands. In another embodiment, $L^A$ and $L^B$ may comprise one or more heteroatoms, for example, nitrogen, silicon, boron, germanium, sulfur and phosphorus, in combination with carbon atoms to form an open, acyclic, or preferably a fused, ring or ring system, for example, a heterocyclopentadienyl ancillary ligand. Other $L^A$ and $L^B$ bulky ligands include but are not limited to porphyrins, phthalocyanines, corrins and other polyazamacrocycles. Independently, each $L^A$ and $L^B$ may be the same or different type of bulky ligand that is bonded to M. In one embodiment of Formula (IV) only one of either $L^A$ or $L^B$ is present.

Independently, each $L^A$ and $L^B$ may be unsubstituted or substituted with a combination of substituent groups R. Non-limiting examples of substituent groups R include one or more from the group selected from hydrogen, or linear, branched alkyl radicals, or alkenyl radicals, alkynyl radicals, cycloalkyl radicals or aryl radicals, acyl radicals, aroyl radicals, alkoxy radicals, aryloxy radicals, alkylthio radicals, dialkylamino radicals, alkoxycarbonyl radicals, aryloxycarbonyl radicals, carbamoyl radicals, alkyl- or dialkyl-carbamoyl radicals, acyloxy radicals, acylamino radicals, aroylamino radicals, straight, branched or cyclic, alkylene radicals, or combination thereof. In a preferred embodiment, substituent groups R have up to 50 non-hydrogen atoms, preferably from 1 to 30 carbon, that can also be substituted with halogens or heteroatoms or the like. Non-limiting examples of alkyl substituents R include methyl, ethyl, propyl, butyl, pentyl, hexyl, cyclopentyl, cyclohexyl, benzyl or phenyl groups and the like, including all their isomers, for example, tertiary butyl, isopropyl and the like. Other hydrocarbyl radicals include fluoromethyl, fluoroethyl, difluoroethyl, iodopropyl, bromohexyl chlorobenzyl and hydrocarbyl substituted organometalloid radicals including trimethylsilyl, trimethylgermyl, methyldiethylsilyl and the like; and halocarbyl-substituted organometalloid radicals including tris(trifluoromethyl)-silyl, methylbis(difluoromethyl)silyl, bromomethyldimethylgermyl and the like; and disubstituted boron radicals including dimethylboron for example; and disubstituted pnictogen radicals including dimethylamine, dimethylphosphine, diphenylamine, methylphenylphosphine, chalcogen radicals including methoxy, ethoxy, propoxy, phenoxy, methylsulfide and ethylsulfide. Non-hydrogen substituents R include the atoms carbon, silicon, boron, aluminum, nitrogen, phosphorus, oxygen, tin, sulfur, germanium and the like, including olefins such as, but not limited to, olefinically unsaturated substituents including vinyl-terminated ligands, for example but-3-enyl, prop-2-enyl, hex-5-enyl and the like. Also, at least two R groups, preferably two adjacent R groups, are joined to form a ring structure having from 3 to 30 atoms selected from carbon, nitrogen, oxygen, phosphorus, silicon, germanium, aluminum, boron or a combination thereof. Also, a substituent group R group such as 1-butanyl may form a carbon sigma bond to the metal M.

Other ligands may be bonded to the metal M, such as at least one leaving group Q. For the purposes of this patent specification and appended claims, the term "leaving group" is any ligand that can be abstracted from a bulky ligand metallocene catalyst compound to form a bulky ligand metallocene catalyst cation capable of polymerizing one or more olefin(s). In an embodiment, Q is a monoanionic labile ligand having a sigma-bond to M. Depending on the oxidation state of the metal, the value for n is 0, 1, or 2 or such that Formula (IV) above represents a neutral bulky ligand metallocene catalyst compound.

Non-limiting examples of Q ligands include weak bases such as amines, phosphines, ethers, carboxylates, dienes, hydrocarbyl radicals having from 1 to 20 carbon atoms, hydrides or halogens and the like or a combination thereof. In another embodiment, two or more Q's form a part of a fused ring or ring system. Other examples of Q ligands include those substituents for R as described above and including cyclobutyl, cyclohexyl, heptyl, tolyl, trifluoromethyl, tetramethylene, pentamethylene, methylidene, methoxy, ethoxy, propoxy, phenoxy, bis(N-methylanilide), dimethylamide, dimethylphosphide radicals and the like.

In another embodiment, the organoaluminum compound of the invention is utilized with the bulky ligand metallocene catalyst compounds of Formula (V) where $L^A$ and $L^B$ are bridged to each other by at least one bridging group, A, as represented in Formula V:

$$L^A A L^B M Q_n \quad \text{(Formula V).}$$

These bridged compounds are known as bridged, bulky ligand metallocene catalyst compounds. $L^A$, $L^B$, M, Q and n are defined above. Non-limiting examples of bridging group A include bridging groups containing at least one Group 13 to 16 atom, often referred to as divalent moiety such as but not limited to at least one of a carbon, oxygen, nitrogen, silicon, aluminum, boron, germanium and tin atom or a combination thereof. Preferably bridging group A contains a carbon, silicon or germanium atom, most preferably A contains at least one silicon atom or at least one carbon atom. The bridging group may also contain substituent groups R as defined above including halogens and iron. Non-limiting examples of bridging group A may be represented by $R'_2C$, $R'_2Si$, $R'_2SiR'_2Si$, $R'_2Ge$, $R'P$, where R' is independently, a radical group which is hydride, hydrocarbyl, substituted hydrocarbyl, halocarbyl, substituted halocarbyl, hydrocarbyl-substituted organometalloid, halocarbyl-substituted organometalloid, disubstituted boron, disubstituted pnictogen, substituted chalcogen, or halogen or two or more R' may be joined to form a ring or ring system. In one embodiment, the bridged, bulky ligand metallocene catalyst compounds of Formula (V) have two or more bridging groups A, see for example EP 664 301 B1. In another embodiment of the invention A is represented by the formula $(Ra)_2 J$, where J is one or more of C, Si, Ge, N or P, and each Ra is, independently, hydrogen, halogen, $C_1$ to $C_{20}$ hydrocarbyl or a $C_1$ to $C_{20}$ substituted hydrocarbyl, where the Ra groups may form a cyclic or fused ring structure.

In another embodiment, the organoaluminum compound of the invention may be utilized with bulky ligand metallocene catalyst compounds where the R substituents on the bulky ligands $L^A$ and $L^B$ of Formulas (IV) and (V) are substituted with the same or different number of substituents on each of the bulky ligands. In another embodiment, the bulky ligands $L^A$ and $L^B$ of formulas (IV) and (V) are different from each other.

In another embodiment, the organoaluminum compound of the invention may be utilized with other bulky ligand metallocene catalyst compounds such as those described in U.S. Pat. Nos. 5,064,802, 5,145,819, 5,243,001, 5,239,022, 5,276,208, 5,296,434, 5,321,106, 5,329,031, 5,304,614, 5,677,401, 5,723,398, 5,753,578, 5,854,363, 5,856,547, 5,858,903, 5,859,158, 5,900,517 and 5,939,503 and PCT publications WO 93/08221, WO 93/08199, WO 95/07140, WO 98/11144, WO 98/41530, WO 98/41529, WO 98/46650, WO 99/02540 and WO 99/14221 and European publications EP-A-0 578 838, EP-A-0 638 595, EP-B-0 513 380, EP-A1-0 816 372, EP-A2-0 839 834, EP-B1-0 632 819, EP-B1-0 748 821 and EP-B1-0 757 996, all of which are fully incorporated herein by reference.

In another embodiment, the organoaluminum compound of the invention may be utilized with bulky ligand metallocene catalysts which include bridged heteroatom, monobulky ligand metallocene compounds. These types of catalysts and catalyst systems are described in, for example, PCT publications WO 92/00333, WO 94/07928, WO 91/04257, WO 94/03506, WO 96/00244, WO 97/15602 and WO 99/20637 and U.S. Pat. Nos. 5,057,475, 5,096,867, 5,055,438, 5,198,401, 5,227,440, and 5,264,405 and European publication EP-A-0 420 436, all of which are herein fully incorporated by reference.

In this embodiment, the organoaluminum compounds of the invention may be utilized with a bulky ligand metallocene catalyst compound represented by Formula VI:

$$L^c A J M Q_n \quad \text{(Formula VI)}$$

where M is a Group 3 to 12 metal atom or a metal selected from the Group of actinides and lanthanides of the Periodic Table of the Elements, preferably M is a Group 4 to 12 transition metal, and more preferably M is a Group 4, 5 or 6 transition metal, and most preferably M is Group 4 transition metal in any oxidation state, especially Ti or Zr or Hf; $L^c$ is a substituted or unsubstituted bulky ligand bonded to M; J is bonded to M; A is bonded to $L^c$ and J; J is a heteroatom ancillary ligand; A is a bridging group; Q is a univalent anionic ligand; and n is the integer 0, 1 or 2. In Formula (VI) above, $L^c$, A and J form a fused ring system. In an embodiment, $L^c$ of formula (VI) is as defined above for $L^A$, A, M and Q of formula (VI) are as defined above in formula (V).

In Formula (VI) J is a heteroatom containing ligand in which J is an element with a coordination number of three from Group 15 or an element with a coordination number of two from Group 16 of the periodic Table of the Elements. Preferably J contains a nitrogen, phosphorus, oxygen or sulfur atom with nitrogen being most preferred. Preferably J is a heteroatom ligand represented by the formula: $JR'_{z-1-y}$, in which J is an element with a coordination number of three from Group 15 or an element with a coordination number of two from Group 16 of the Periodic Table of Elements, each R' is, independently, a radical selected from a group consisting of $C_1$-$C_{20}$ hydrocarbyl radicals, substituted $C_1$-$C_{20}$ hydrocarbyl radicals, wherein one or more hydrogen atoms is replaced by a halogen atom, an amido radical, a phosphido radical, an alkoxy radical or any other radical containing a Lewis acidic or basic functionality, and "z" is the coordination number of the element J.

In another embodiment, the organoaluminum compound of the invention is utilized with a bulky ligand metallocene catalyst compound which is a complex of a metal, preferably a transition metal, a bulky ligand, preferably a substituted or unsubstituted pi-bonded ligand, and one or more heteroallyl moieties, such as those described in U.S. Pat. Nos. 5,527,752 and 5,747,406 and EP-B1-0 735 057, all of which are herein fully incorporated by reference.

In another embodiment the organoaluminum compound of the invention is utilized with a ligand metallocene catalyst compound, which may be represented by Formula (VII):

$$L^D M Q_2 (YZ) X_n \quad \text{Formula (VII)}$$

where M is a Group 3 to 16 metal, preferably a Group 4 to 12 transition metal, and most preferably a Group 4, 5 or 6 transition metal; $L^D$ is a bulky ligand that is bonded to M; each Q is independently bonded to M and $Q_2(YZ)$ forms a unicharged polydentate ligand; Q is a univalent anionic ligand also bonded to M; X is a univalent anionic group when n is 2 or X is a divalent anionic group when n is 1; n is 1 or 2.

In Formula (VII), $L^D$ is defined to be the same as $L^A$ above and M are as defined above for Formula (IV). Q is as defined above for Formula (IV), preferably Q is selected from the group consisting of —O—, —NR—, —$CR_2$— and —S—; Y is either C or S; Z is selected from the group consisting of —OR, —NR$_2$, —CR$_3$, —SR, —SiR$_3$, —PR$_2$ and —H, and substituted or unsubstituted aryl groups, with the proviso that when Q is —NR— then Z is selected from one of the group consisting of —OR, —NR$_2$, —SR, —SiR$_3$, —PR$_2$ and —H; R is selected from a group containing carbon, silicon, nitrogen, oxygen, and/or phosphorus, preferably where R is a hydrocarbon group containing from 1 to 20 carbon atoms, most preferably an alkyl, cycloalkyl, or an aryl group; n is an integer from 1 to 4, preferably 1 or 2; X is a univalent anionic group when n is 2 or X is a divalent anionic group when n is 1; preferably X is a carbamate, carboxylate, or other heteroallyl moiety described by the Q, Y and Z combination.

In another embodiment, the organoaluminum compound of the invention is utilized with a bulky ligand metallocene catalyst compounds, which include heterocyclic ligand complexes where the bulky ligands, the ring(s) or ring system(s), include one or more heteroatoms or a combination thereof. Non-limiting examples of heteroatoms include a Group 13 to 16 element, preferably nitrogen, boron, sulfur, oxygen, aluminum, silicon, phosphorus and tin. Examples of these bulky ligand metallocene catalyst compounds are described in WO 96/33202, WO 96/34021, WO 97/17379 and WO 98/22486 and EP-A1-0 874 005 and U.S. Pat. Nos. 5,637,660, 5,539,124, 5,554,775, 5,756,611, 5,233,049, 5,744,417, and 5,856,258 all of which are herein incorporated by reference.

In another embodiment, the organoaluminum compound of the invention may be utilized with a bulky ligand metallocene catalyst compounds, which include complexes known as transition metal catalysts based on bidentate ligands containing pyridine or quinoline moieties, such as those described in U.S. application Ser. No. 09/103,620 filed Jun. 23, 1998, which is herein incorporated by reference. In another embodiment, the bulky ligand metallocene catalyst compounds are those described in PCT publications WO 99/01481 and WO 98/42664, which are fully incorporated herein by reference.

In another embodiment, the organoaluminum compound of the invention may be utilized with a bulky ligand metallocene catalyst compounds which may be represented by Formula (VIII):

$$((Z)XA_t(YJ))_qMQ_n \quad \quad \text{Formula (VIII)}$$

where M is selected from Group 3 to 13 or lanthanide and actinide series of the Periodic Table of the Elements; Q is bonded to M and each Q is a monovalent, bivalent, or trivalent anion; X and Y are bonded to M; one or more of X and Y are heteroatoms, preferably both X and Y are heteroatoms; Y is contained in a heterocyclic ring J, where J comprises from 2 to 50 non-hydrogen atoms, preferably 2 to 30 carbon atoms; Z is bonded to X, where Z comprises 1 to 50 non-hydrogen atoms, preferably 1 to 50 carbon atoms, preferably Z is a cyclic group containing 3 to 50 carbon atoms, preferably 3 to 30 carbon atoms; t is 0 or 1; when t is 1, A is a bridging group joined to at least one of X, Y or J, preferably X and J; q is 1 or 2; n is 1, 2, 3, or 4 depending on the oxidation state of M. In one embodiment, where X is oxygen or sulfur then Z is optional. In another embodiment, where X is nitrogen or phosphorus then Z is present. In an embodiment, Z is preferably an aryl group, more preferably a substituted aryl group.

It is also within the scope of this invention, in one embodiment, that the bulky ligand metallocene catalyst compounds, which may be utilized with the organoaluminum compound of the invention include complexes of Ni$^{2+}$ and Pd$^{2+}$ described in the articles Johnson, et al., "New Pd(II)- and Ni(II)-Based Catalysts for Polymerization of Ethylene and α-Olefins", J. Am. Chem. Soc. 1995, 117, pp. 6414-6415 and Johnson, et al., "Copolymerization of Ethylene and Propylene with Functionalized Vinyl Monomers by Palladium(II) Catalysts", J. Am. Chem. Soc., 1996, 118, pp. 267-268, and WO 96/23010 published Aug. 1, 1996, WO 99/02472, U.S. Pat. Nos. 5,852,145, 5,866,663, and 5,880,241, which are all herein fully incorporated by reference. These complexes can be either dialkyl ether adducts, or alkylated reaction products of the described dihalide complexes that can be activated to a cationic state by the activators of this invention described below.

Also included as bulky ligand metallocene catalysts are those diimine based ligands of Group 8 to 10 metal compounds disclosed in PCT publications WO 96/23010 and WO 97/48735 and Gibson, et al., Chem. Comm., pp. 849-850 (1998), all of which are herein incorporated by reference.

Other bulky ligand metallocene catalysts, which may be utilized with the organoaluminum compound of the invention, are those Group 5 and 6 metal imido complexes described in EP-A2-0 816 384 and U.S. Pat. No. 5,851,945, which are incorporated herein by reference. In addition, bridged bis(amido) catalyst compounds are described in WO 96/27439, which is herein incorporated by reference. Other bulky ligand metallocene catalysts are described as bis(hydroxy aromatic nitrogen ligands) in U.S. Pat. No. 5,852,146 which is incorporated herein by reference. Other metallocene catalysts containing one or more Group 15 atoms include those described in WO 98/46651, which is herein incorporated by reference. Still another bulky ligand metallocene catalyst includes those multinuclear bulky ligand metallocene catalysts as described in WO 99/20665, which is incorporated herein by reference.

It is also contemplated that in one embodiment, the bulky ligand metallocene catalysts of the invention described above include their structural or optical or enantiomeric isomers (meso and racemic isomers, for example see U.S. Pat. No. 5,852,143, incorporated herein by reference) and mixtures thereof.

In a preferred embodiment of the invention, the metallocene catalyst compound is one or more of: dimethylsilyl bis-(2-methyl-4-phenylindenyl)zirconium dichloride, dimethylsilyl bis(indenyl)hafnium dimethyl; dimethylsilanediyl-(2-methyl-4-(4'-tert-butylphenyl)indenyl(2-isopropyl-4-(4'-tert-butylphenyl)indenyl)zirconium dichloride, bis(1,3-methyl,n-butyl-cyclopentadienyl)zirconium dichloride, bis (1,3-methyl,n-butyl-cyclopentadienyl)zirconium dimethyl, dimethylsilylbis(2-methyl-indenyl)zirconium dichloride, dimethylsilyl bis(2-methyl-indenyl)zirconium dimethyl, dimethylsilyl bis(2-methyl,4,6-dipropyl-indenyl)zirconium dichloride; dimethylsilyl bis(2-methyl,4,6-dipropyl-indenyl) zirconium dimethyl; dimethylsilyl bis(2-methyl,4-phenyl-indenyl)zirconium dimethyl; dimethylsilyl bis(2-methyl,4-naphthyl-indenyl)zirconium dichloride; dimethylsilyl bis(2-methyl,4-naphthyl-indenyl)zirconium dimethyl; dimethylsilyl bis(2-ethyl,4-phenyl-indenyl)zirconium dichloride; dimethylsilyl bis(2-ethyl,4-phenyl-indenyl)zirconium dimethyl; dimethylsilyl bis(2-methyl,4-(di-tert-butyl-phenyl)-indenyl)zirconium dichloride; dimethylsilyl bis (2-methyl,4-(di-tert-butyl-phenyl)-indenyl)zirconium dimethyl, dimethylsilyl bis(2-methyl-indenyl)hafnium dichloride, dimethylsilyl bis(2-methyl-indenyl)hafnium dimethyl, dimethylsilyl bis(2-methyl,4,6-dipropyl-indenyl) hafnium dichloride; dimethylsilyl bis(2-methyl,4,6-dipropyl-indenyl)hafnium dimethyl; dimethylsilyl bis(2-methyl,4-phenyl-indenyl)hafnium dichloride; dimethylsilyl bis(2-methyl,4-phenyl-indenyl)hafnium dimethyl; dimethylsilyl bis(2-methyl,4-naphthyl-indenyl)hafnium dichloride; dimethylsilyl bis(2-methyl,4-naphthyl-indenyl)hafnium dimethyl; dimethylsilyl bis(2-ethyl,4-phenyl-indenyl)hafnium dichloride; dimethylsilyl bis(2-ethyl,4-phenyl-indenyl) hafnium dimethyl; dimethylsilyl bis(2-methyl,4-(di-tert-butyl-phenyl)-indenyl)hafnium dichloride; and dimethylsilyl bis(2-methyl,4-(di-tert-butyl-phenyl)-indenyl)hafnium dimethyl.

Non-limiting examples of catalyst compounds useful herein include: $Me_2Si(ind)_2MX_2$, $Me_2Si(ind)_2MX_2$, $Me_2Si(2-Me-4-Ph-Ind)_2MX_2$, $Me_2Si(2-Me-benzindenyl)_2MX_2$, $Me_2Si(2-Me-Ind)_2MX_2$, $Me_2Si(2-Me-Ind)_2MX_2$, $Me_2Si(2-Me-4-naphthyl-indenyl)_2MX_2$, ethylene-bis$(Ind)_2MX_2$, $Me_2Si(2-Me-4-(2'-Me-Ph)-Ind)_2MX_2$, $Me_2Si(2-Me-4-(4'-Me-Ph)-Ind)_2MX_2$, $Me_2Si(2-methyl-4-(4'-t-Bu-Ph)-Ind)_2MX_2$, $Me_2Si(2-Me-4-(4'-t-Bu-Ph)-Ind)2-iPr-4-(4'-t-Bu-Ph-Ind)_2MX_2$, $Me_2Si(2-Me-4,6-iPr_2-Ind)_2MX_2$, $(Cp)_2MX_2$, $(Me_5Cp)_2MX_2$, $(Cp)(Me_5Cp)_2MX_2$, $(1-Me,4-Bu-Cp)_2MX_2$, $(1-Me,4-EtCp)_2MX_2$, $(1-Me,4-BzCp)_2MX_2$, $(1-Me,3-n-PrCp)_2MX_2$, $(1-Me,3-iPrCp)_2MX_2$, $(1,3-Me_2Cp)_2MX_2$, $(n-PrCp)_2MX_2$, $(n-BuCp)_2MX_2$, $(t-BuCp)_2MX_2$, $(BzCp)_2MX_2$, $(BzCp)(Me_5Cp)_2MX_2$, $(BzCp)(Me_5Cp)_2MX_2$, $(PrCp)(Me_5Cp)_2MX_2$, $(PrCp)(Me_4Cp)_2MX_2$, $(PrCp)(Me_4Cp)_2MX_2$, $(Me_4,PrCp)(Me_5Cp)_2MX_2$, $(Me_4,PrCp)(Cp)_2MX_2$, $Me_2Si(Cp)_2MX_2$, $Me_2Si(Cp)(Me_5Cp)_2MX_2$, $Me_2Si(1-Me,4-butylCp)_2MX_2$, $Me_2Si(1-Me,4-EtCp)_2MX_2$, $Me_2Si(1-Me,4-BzCp)_2MX_2$, $Me_2Si(1-Me,3-butylCp)_2MX_2$, $Me_2Si(1-Me,3-n-PrCp)_2MX_2$, $Me_2Si(1-Me,3-i-PrCp)_2MX_2$, $Me_2Si(1,3-Me_2Cp)_2MX_2$, $Me_2Si(n-PrCp)_2MX_2$, $Me_2Si(n-BuCp)_2MX_2$, $Me_2Si(t-Bu)(Cp)_2MX_2$, $Me_2Si(BzCp)_2MX_2$, $Me_2Si(BzCp)(Me_5Cp)_2MX_2$, $Me_2Si(PrCp)(Me_4Cp)_2MX_2$, $Me_2Si(Me_4,PrCp)(Me_5Cp)_2MX_2$, $Me_2Si(Me_4,PrCp)(Cp)_2MX_2$, and $Me_2Si(Me_4,PrCp)(Cp)_2MX_2$, where M is Hf or Zr and X is Cl, Me, —OMe, Bz, F, or amide, preferably M is Zr and X is Me, preferably M is Zr and X is Cl, preferably M is Hf and X is Me, preferably M is Hf and X is Cl.

Additional useful catalyst compounds can be found at column 11, line 1 to column 15, line 46 of U.S. Pat. No. 8,022,005.

Solid Support Materials

Preferred ion-exchange layered silicate useful in the present invention are silicate compounds having crystal structures wherein layers formed by strong ionic and covalent bonds are laminated in parallel with weak ionic bonding, and the ions contained between the layers are exchangeable. Most ion-exchange layered silicates naturally occur as the main component of clay minerals, but these ion-exchange layered silicates may be artificially synthesized materials. Preferred ion-exchange layered silicates useful in this invention include natural or synthetic montmorillonite, nontronite, beidellite, volkonskoite, laponite, hectorite, saponite, sauconite, stevensite, vermiculite, halloysite, aluminate oxides, bentonite, kaolinite, dickite, smectic clays, mica, magadiite, kenyaite, octosilicate, kanemite, makatite, attapulgite, sepiolite, zeolitic layered materials (such as ITQ-2, MCM-22, and ferrierite precursors) and mixtures thereof. In a preferred embodiment, the ion-exchange layered silicate is acidified by contacting with an acid (such as sulfuric acid, hydrochloric acid, a carboxylic acid, an amino acid, or the like.)

Preferred ion-exchange layered silicates useful in this invention include those having a 1:1 type structure or a 2:1 type structure. Examples of the ion-exchange layered silicate include layered silicates having a 1:1 type structure or a 2:1 type structure as described in "Clay Mineralogy" written by R. E. Grim (published by McGraw Hill in 1968) and "Chemistry of Clays and Clay Minerals" written by A. C. Newman (published by John Wiley and Sons: New York in 1987). The 1:1 type structure is a structure formed by laminating 1:1 layered structures having one layer of tetrahedral sheet and one layer of octahedral sheet combined as described in the above literature "Clay Mineralogy", and the 2:1 type structure is a structure formed by laminating 2:1 layered structures having one layer of octahedral sheet sandwiched between two layers of tetrahedral sheets. Examples of ion-exchange layered silicate comprising the 1:1 layer as the main constituting layer include kaolin group silicates such as dickite, nacrite, kaolinite, metahalloysite, halloysite or the like, and serpentine group silicates such as chrysotile, lizardite, antigorite or the like. Examples of ion-exchange layered silicate comprising the 2:1 layer as the main constituting layer include smectite group silicates such as montmorillonite, beidellite, nontronite, saponite, hectorite, stephensite or the like, vermiculite group silicates such as vermiculite or the like, mica group silicates such as mica, illite, sericite, glauconite or the like, and attapulgite, sepiolite, palygorskite, bentonite, pyrophyllite, talc, chlorites and the like. Mixed layer silicates are also included. In some embodiments, an ion-exchange layered silicate having the 2:1 type structure is preferable. In another preferred embodiment, a smectite group silicate is used and in a particularly preferable example the ion exchange layered silicate comprises montmorillonite.

Chemical Treatment of Ion-Exchange Layered Silicate

The chemical treatment of an ion-exchange layered silicate is carried out by bringing it in contact with an acid, a salt, an alkali, an oxidizing agent, a reducing agent or a treating agent containing a compound intercalatable between layers of an ion-exchange layered silicate. The intercalation means to introduce other material between layers of a layered material, and the material to be introduced is called a guest. Among these treatments, acid treatment or salt treatment is particularly preferable.

A common effect achieved by chemical treatment is to exchange an intercalation cation with other cations, and in addition to this effect, the following various effects can be achieved by various chemical treatments. For example, acid treatment removes impurities on the surface of silicate, and cations such as Al, Fe, Mg or the like, in a crystal structure are eluted, thereby increasing the surface area. This treatment enhances the acid strength and acidity of the layered silicate.

Alkali treatment destroys a crystal structure of a clay mineral, and changes a structure of the clay mineral. Also, intercalation or salt treatment forms an ion composite, a molecule composite, an organic derivative or the like, and changes a surface area or a distance between layers. By using an ion-exchange reaction, an exchangeable intercalated cation between layers can be replaced by other large bulky ions, thereby producing a layered material having the distance between layers enlarged. Thus, the bulky ions have a function as a column supporting the layered structure, and are called pillars.

In embodiments of the invention, one, two, three, or more kinds of members selected from the group consisting of acids, salts, alkalis, oxidizing agents, reducing agents and compounds intercalatable between layers of an ion-exchange layered silicate may be combined and used as treating agents. Also, acids, salts, alkalis, oxidizing agents, reducing agents and compounds intercalatable between layers of an ion-exchange layered silicate may be respectively used in a combination of two or more members. Among them, a combination of a salt treatment and an acid treatment is particularly preferable.

The above-mentioned various treating agents may be used as a treating agent solution by dissolving in an appropriate solvent, or it is possible to use a treating agent itself as a solvent. Examples of a usable solvent include water, alcohols, aliphatic hydrocarbons, aromatic hydrocarbons, esters, ethers, ketones, aldehydes, furans, amines, dimethylsulfoxide, dimethylformamide, carbon disulfide, nitrobenzene, pyridines or their halides. A concentration of a treating agent in a treating agent solution is preferably from 0.1 to 100 wt. %, more preferably from 5 to 50 wt. %. If the treating agent concentration is within these ranges, a time required for treatment becomes shorter and an efficient production is possible.

Chemical Treatment Protocol
Acid Treatment

An acid treatment removes impurities on the surface or ion-exchanges a cation present between layers, and in addition to this function, the acid treatment elutes a part or whole of cations such as Al, Fe, Mg or the like in a crystal structure. Examples of an acid used in acid treatment include hydrochloric acid, nitric acid, sulfuric acid, phosphoric acid, acetic acid, and oxalic acid and the like. Particularly, it is preferable to use an inorganic acid. Usually the acid is used in a form of an acid aqueous solution. The acid used in the treatment may be a mixture of at least two kinds of acids. In a preferred embodiment, the acid used herein is sulfuric acid.

A particular preferable embodiment of the present invention is to carry out a treatment with an acid having a specific concentration. Any concentration of acid may be used, however higher acid concentrations (and higher temperatures) are more efficient. In particular using an acid concentration of more than 5 weight % (based upon the weight of the acid, any liquid diluent or solvent and the ion exchange layered silicate present), preferably more than 10 weight %, more preferably more than 15 weight % has been found to be effective. In a preferred embodiment, the treatment is performed at temperatures of more than 50° C., preferably more than 70° C., more preferably at more than 90° C. The treatment preferably is allowed to react for 5 minutes to 10 hours, more preferably 30 minutes to 8 hours, more preferably 1 to 6 hours. In a particularly preferred embodiment, the treatment occurs at 90° C. or more for 2 to 6 hours using an acid concentration of more than 15 weight %. In another particularly preferred embodiment, the treatment occurs at 100° C. or more for 2 to 4 hours using an acid concentration of more than 15 weight %.

An acid used for the concentrated acid treatment may be the same as those used in an ordinary acid treatment, but is preferably sulfuric acid, nitric acid or hydrochloric acid, more preferably sulfuric acid.

Salt Treatment

Further, one may carry out a salt treatment. The salt treatment means a treatment carried out for the purpose of exchanging cations in an ion-exchange layered silicate. The treating conditions with a salt are not specifically limited, but it is preferable to carry out the salt treatment under conditions of a salt concentration of from 0.1 to 50 wt. %, a treating temperature of from room temperature to a boiling point and a treating time of from 5 minutes to 24 hours in such a manner as to elute at least a part of materials constituting an ion-exchange layered silicate. Also, the salt may be used in an organic solvent such as toluene, n-heptane, ethanol or the like, or may be used in the absence of a solvent if it is liquid-like at the treating temperature, but it is preferably used as an aqueous solution. However, depending on the kind of a salt employed, the salt treatment achieves an effect similar to an acid treatment.

In preferred embodiments of the invention, one can ion exchange at least 40%, preferably at least 60% of ion exchangeable cations of Group 1 metals contained in an ion-exchange layered silicate with cations dissociated from the salts as described above. After carrying out the above chemical treatment, it is preferable to remove ions eluted from the treatment and an excess amount of a treating agent. For this operation, water or an organic solvent is generally used. After dehydrating, drying is carried out generally at a drying temperature of from 100 to 800° C., preferably from 150 to 600° C.

Drying of Chemically Treated Ion-Exchange Layered Silicate

These ion-exchange layered silicates can change their properties depending on a drying temperature employed even when their structures are not destroyed, and it is therefore preferable to change a drying temperature depending on their uses. The drying period is usually in a range of from 1 minute to 24 hours, preferably from 5 minutes to 6 hours, and a drying atmosphere is preferably dry air, dry nitrogen, dry argon, or carried out under reduced pressure. A drying method is not specifically limited, but various methods may be employed.

Pore Size/Distribution

The evaluation of the pore size distribution useful herein employs the desorption isotherm (by nitrogen adsorption-desorption method). The desorption isotherm is a curve obtained while reducing the relative pressure. The desorption isotherm shows a lower relative pressure to the same desorbed gas amount as compared with adsorption isotherm, and consequently shows a lower free energy state, and is generally considered to be closer to a state of real thermodynamic stability.

In one embodiment, an ion-exchange layered silicate with any pore size and or any pore size distribution may be used. In another embodiment, included in this invention is the preferred pore size distributions of the ion-exchange layered silicate as described in US 2003/0027950 A1. Where $D_m$ (from differential values of pore volumes) represents a pore size diameter showing a maximum peak intensity and is generally expressed as "most frequently appearing pore diameter", $D_{VM}$ represents a maximum peak intensity and $D_{m1/2}$ represents a pore size diameter on the smaller diameter side corresponding to a point, the peak intensity of which is ½ of the maximum peak intensity. A pore diameter $D_{m1/2}$ is present at least one respectively on both sides of $D_m$, i.e., on the larger diameter side of $D_m$ and on the smaller diameter side of $D_m$, but a value on the smaller diameter side is taken as the $D_{m1/2}$ value in the present invention. Also, if there are a plurality of $D_{m1/2}$ values on the smaller diameter side, the largest value is employed for calculation. In one embodiment of the invention, the $D_{m1/2}/D_m$ can range from 0.1 to 0.9. In another embodiment, a $D_{m1/2}/D_m$ value is preferably at least 0.68, more preferably at least 0.70.

An ion-exchange layered silicate may have a predetermined pore size, but its pore size is sufficiently large to accept a metallocene complex, an organoaluminum compound, and a monomer. Accordingly, these compounds participating in the reaction easily enter into pores in respective stages of formation of a catalyst, activation, prepolymerization and polymerization, and complexes are highly dispersed in carriers, and consequently metallocene catalyst active sites are uniformly formed. In a preferred embodiment, the ion exchange layered silicate has a pore size that is sufficiently large enough that the catalyst compound and the organoaluminum may freely enter and diffuse evenly within the particle. Preferred pore sizes include 40 Angstroms to 500 Angstroms, preferably 50 Angstroms to 300 Angstroms, more preferably 70 to 200 Angstroms.

Carrier Strength

In one embodiment, the ion exchange layered silicate may have a compression fracture strength (also called average crushing strength) as measured by a minute compression tester of 3 to 20 MPa. Preferably, the average crushing strength is at least 5 MPa, more preferably at least 7 MPa. In addition, the upper limit of the ion exchange layered silicate strength is preferably an average crushing strength of at most 20 MPa, more preferably at most 18 MPa.

Olefin Polymerization Catalyst System

In the present invention, an olefin polymerization catalyst system can be prepared by contacting the organoaluminum compounds described herein with a catalyst compound (also called catalyst precursor compounds, pre-catalyst compounds or catalyst precursors). In one embodiment, a supported catalyst system may be prepared, generally, by the reaction of the organoaluminum compound with the addition of a metallocene catalyst, followed by addition of an ion-exchange layered silicate. Alternately, a supported catalyst system may be prepared, generally, by the reaction of the organoaluminum compound, an ion-exchange layered silicate, and then adding one or more metallocene catalysts.

In a preferred embodiment, the ion exchange layered silicate is combined with the organoaluminum and thereafter is combined with the catalyst.

Contact between an ion-exchange layered silicate and an organoaluminum compound and/or metallocene can be carried out under an inert gas atmosphere such as nitrogen in a solvent of an inert hydrocarbon such as hexane, heptane, pentane, cyclohexane, benzene, toluene, xylene or the like, and the solvent may be used alone or in a mixture of two or more.

An amount of an organoaluminum compound used is preferably from 0.01 to 1000 mmol, more preferably from 0.1 to 100 mmol, per 1 g of an ion-exchange layered silicate.

A concentration of an ion-exchange layered silicate in a solvent is preferably from 0.001 to 100 g/mL, more preferably form 0.01 to 10 g/mL, and a concentration of an organoaluminum compound is preferably from 0.001 to 100 mmol/mL, more preferably from 0.01 to 10 mmol.

Contacting may be carried out by dispersing an ion-exchange layered silicate in a solvent and then bringing an organoaluminum compound in contact therewith. Alternatively, contacting may be carried out by adding an organoaluminum compound to a solvent and then dispersing an ion-exchange layered silicate therein.

The contacting treatment is carried out generally at a temperature of from −50° C. to a boiling point of a solvent, preferably from 0° C. to a boiling point of a solvent. The contacting time is from 1 minute to 48 hours, preferably from 1 minute to 24 hours.

The order of contacting an organoaluminum compound with an ion-exchange layered silicate is not specifically limited as far as the object of the present invention is achieved, but it is more effective to carry out the contacting treatment after chemical treatment of the silicate or preferably after drying carried out after the chemical treatment.

Also, the order of contacting treatment step of an organoaluminum compound and an ion-exchange layered silicate and the granulation step of an ion-exchange layered silicate is not specifically limited as far as the object of the present invention is achieved, but it is preferable to carry out the treatment with an organoaluminum compound after granulating the silicate.

Further, it is possible to enhance the effect of the present invention by combining the above-mentioned respective treatments. Thus, after controlling a particle size distribution and a carrier particle strength by granulating an ion-exchange layered silicate, a carrier obtained through the following Step 1 and Step 2 is used as a catalyst component for olefin polymerization.

Step 1: after granulating an ion-exchange layered silicate, the silicate is treated with an acid having an acid concentration as described above.

Step 2: after carrying out step 1, the silicate is treated with an organoaluminum compound which is any organoaluminum compound from the discussion above.

A metallocene can be added with, prior to, or after the silicate is treated with an organoaluminum compound.

Polymerization Process and Olefin Monomers

The organoaluminum compounds of the invention and catalyst systems utilizing the organoaluminum compounds described above are suitable for use in any prepolymerization and/or polymerization process over a wide range of temperatures and pressures. The temperatures may be in the range of from −60° C. to about 280° C., preferably from 50° C. to about 200° C. In another embodiment, the polymerization temperature is above 0° C., above 50° C., above 80° C., above 100° C., above 150° C. or above 200° C. In one embodiment, the pressures employed may be in the range from 1 atmosphere to about 500 atmospheres or higher.

Polymerization processes include solution, gas phase, slurry phase and a high pressure process or a combination thereof. Particularly preferred is a gas phase or slurry phase polymerization of one or more olefins) at least one of which is ethylene or propylene.

In one embodiment, the process of the invention is directed toward a solution, high pressure, slurry or gas phase polymerization process of one or more olefin monomers having from 2 to 30 carbon atoms, preferably 2 to 12 carbon atoms, and more preferably 2 to 8 carbon atoms. The invention is particularly well suited to the polymerization of two or more olefin monomers of ethylene, propylene, butene-1, pentene-1, 4-methyl-pentene-1, hexene-1, octene-1 and decene-1.

Other monomers useful in the process of the invention include ethylenically unsaturated monomers, diolefins having 4 to 18 carbon atoms, conjugated or nonconjugated dienes, polyenes, vinyl monomers and cyclic olefins. Non-limiting monomers useful in the invention may include norbornene, norbornadiene, isobutylene, isoprene, vinylbenzocyclobutane, styrenes, alkyl substituted styrene, ethylidene norbornene, dicyclopentadiene and cyclopentene.

In another embodiment of the process of the invention, a copolymer of ethylene is produced, where with ethylene, a comonomer having at least one alpha-olefin having from 4 to 15 carbon atoms, preferably from 4 to 12 carbon atoms, and most preferably from 4 to 8 carbon atoms, is polymerized in a gas phase process.

In another embodiment of the process of the invention, ethylene or propylene is polymerized with at least two different comonomers, optionally one of which may be a diene, to form a terpolymer.

In one embodiment, the invention is directed to polymerization process, particularly a gas phase or slurry phase process, for polymerizing propylene alone or with one or more other monomers including ethylene, and/or other olefins having from 4 to 12 carbon atoms.

In embodiments of the process of this invention, the catalyst system may be employed in liquid phase (solution, slurry, suspension, bulk phase or combinations thereof), in high pressure liquid, or supercritical fluid or gas phase processes. Each of these processes may be employed in single, parallel or series reactors. The liquid processes comprise contacting the ethylene and/or α-olefin and at least one vicinally disubstituted olefin monomer with the catalyst system described herein in a suitable diluent or solvent and allowing the monomers to react for a sufficient time to produce embodiments of the invention copolymers. One or more of the monomers used in the polymerization may be utilized as a solvent and/or diluent, generally in homogeneous polymerizations in the liquid monomer or monomers. Hydrocarbyl solvents are also suitable, both aliphatic and aromatic, including hexane and toluene. Bulk and slurry processes may typically be accomplished by contacting the catalysts with a slurry of liquid monomer, the catalyst system being supported. Gas phase processes may use the supported catalyst and may be conducted in any manner known to be suitable for producing ethylene homopolymers or copolymers via coordination polymerization. Illustrative examples may be found in U.S. Pat. Nos. 4,543,399, 4,588,790, 5,028,670, 5,382,638, 5352, 749, 5,436,304, 5,453,471, 5,463,999, and WO 95/07942. Each is incorporated by reference for purposes of U.S. patent practice.

Generally, the polymerization reaction temperature may vary from −50° C. to 250° C. The reaction temperature conditions may be from −20° C. to 220° C., or below 200° C. The pressure may vary from 1 mm Hg to 2500 bar, or from 0.1 bar to 1600 bar, or from 1.0 to 500 bar. Where lower molecular weight copolymers, e.g., $M_n \leq 10,000$, are sought, it may be suitable to conduct the reaction processes at temperatures above 0° C. and pressures under 500 bar.

In a preferred embodiment of the invention herein, any polymerization process is used to polymerize: 1) alpha olefins, i.e. ethylene, propylene, 1-butene, 1-pentene, 1-hexene, 1-heptene, 1-octene, 1-nonene, 1-decene, 1-dodecene, 4-methyl-1-pentene, 5-methyl-1-nonene, 3-methyl-1-pentene, 3,5,5-trimethyl-1-hexene, vinylcyclohexane, or combinations thereof; and or 2) Diolefins such as those described in the literature for ethylene copolymers, including for EPDM rubber, the disclosure of U.S. Pat. No. 5,767,208, i.e., straight chain acyclic diolefins, branched acyclic diolefins, single ring alicyclic diolefins, multi-ring alicyclic fused and bridged ring diolefins, cycloalkenyl-substituted alkenes or combinations thereof. (Examples include 1,4-hexadiene, dicyclopentadiene, 5-ethylidene-2-norbornene, vinylcyclohexene, 5-vinyl-2-norbornene, or combinations thereof.)

Polymer Products

The polymers produced by the process of the invention can be used in a wide variety of products and end-use applications. The polymers produced can be homo- and co-polymers of ethylene and propylene and include linear low density polyethylene, elastomers, plastomers, high-density polyethylenes, medium density polyethylenes, low density polyethylenes, polypropylene and polypropylene copolymers. Polymers, typically ethylene based copolymers, have a density of from 0.86 g/cc to 0.97 g/cc; density being measured in accordance with ASTM-D-1238. Propylene based polymers produced include isotactic polypropylene, atactic polypropylene and random, block or impact copolymers.

The polypropylene homopolymer or propylene copolymer produced herein may have some level of isotacticity, and is preferably isotactic or highly isotactic. As used herein, "isotactic" is defined as having at least 10% isotactic pentads according to analysis by $^{13}$C-NMR as described in US 2008/0045638 at paragraph [0613] et seq. As used herein, "highly isotactic" is defined as having at least 60% isotactic pentads according to analysis by $^{13}$C-NMR. In a desirable embodiment, a polypropylene homopolymer having at least 85% isotacticity, preferably least 90% isotacticity is produced herein. In another embodiment, the propylene polymer produced may be atactic. Atactic polypropylene is defined to be less than 10% isotactic or syndiotactic pentads according to analysis by $^{13}$C-NMR.

In a preferred embodiment of the invention, the catalyst systems herein show a catalyst activity of 250 g polymer/(g cat*hr) or more, preferably 600 g polymer/(g cat*hr) or more, preferably 1000 g polymer/(g cat*hr) or more, preferably 5000 g polymer/(g cat*hr) or more. Alternately, the catalyst systems herein show a catalyst activity of 1500 g polymer/(mmol Zr*hr) or more, preferably 1700 g polymer/(mmol Zr*hr) or more, preferably 2000 g polymer/(mmol Zr*hr), preferably 5000 g polymer/(mmol Zr*hr) or more.

The polymers of embodiments of the invention may have an $M_n$ (number-average molecular weight) value from 300 to 1,000,000, or between from 700 to 300,000 g/mol. For low weight molecular weight applications, such as those copolymers useful in lubricating and fuel oil compositions, an $M_n$ of 300 to 20,000 g/mol is contemplated, or less than or equal to 10,000. Additionally, polymer of embodiments of the invention will typically comprise a molecular weight distribution (Mw/Mn) in the range of $\geq 1$, or $\geq 1.5$ or $\leq 6$, or $\leq 4$ or $\leq 3$, preferably from greater than 1 to 40, alternately from 1.5 to 20, alternately from 1.5 to 10, alternately from 1.5 to 6, alternately from 1.5 to 4, alternately from 2 to 3.

Preferred propylene polymer, preferably homopolymer, produced herein has an Mw of 20,000 up to 2,000,000 g/mol.

For higher molecular weight applications, preferred polymer, preferably homopolymer, produced herein has an Mw of 20,000 up to 2,000,000 g/mol, alternately 50,000 to 1,500,000 g/mol, alternately 100,000 to 1,300,000 g/mol, alternately 300,000 to 1,300,000 g/mol, alternately 500,000 to 1,300,000 g/mol.

Mn is number average molecular weight, Mw is weight average molecular weight, and Mz is z average molecular weight. Molecular weight distribution (MWD) is defined to be Mw divided by Mn. Unless otherwise noted, all molecular weight units (e.g., Mw, Mn, Mz) are g/mol.

The polymers of this invention may be blended and/or coextruded with any other polymer. Non-limiting examples of other polymers include linear low density polyethylenes, elastomers, plastomers, high pressure low density polyethylene, high density polyethylenes, isotactic polypropylene, ethylene propylene copolymers and the like.

Polymers produced by the process of the invention and blends thereof are useful in such forming operations as film, sheet, and fiber extrusion and co-extrusion as well as blow molding, injection molding, and roto-molding. Films include blown or cast films formed by coextrusion or by lamination useful as shrink film, cling film, stretch film, sealing film or oriented films.

In other embodiments, the invention relates to:
1. A composition comprising the reaction product of AlH$_3$ or a trialkyl aluminum and a cyclic vinyl terminated olefin.
2. A composition comprising the reaction product of:
  Al(R)$_3$ and a compound represented by the formula (I):

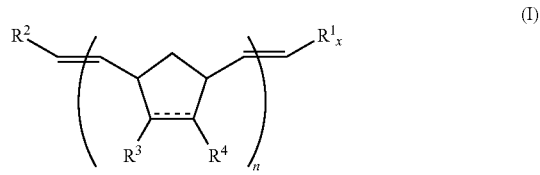

wherein the dotted line indicates an optional double bond;
x is 0 or 1;
the double bonds depicted as trans can each, independently, be cis or trans;
$R^1$ and $R^2$ can be the same or different and each is a hydrogen atom or hydrocarbyl group having from one to twenty carbon atoms;

$R^3$ and $R^4$ can be the same or different and each is a hydrogen atom or a hydrocarbyl group having from one to forty carbon atoms (preferably 1 to 20, preferably 1 to 12, preferably 2 to 6 carbon atoms) or $R^3$ and $R^4$ may be joined together to form a five-membered or six-membered ring, the ring having one or two optional double bonds, provided that at least one of $R^1$ or $R^2$ is a hydrogen atom such that a vinyl end group is present;

n is an integer from 1 to 100 (alternately n is 1, 2, 3, 4, 5, 6, 7, 8, 9, 10, 11, 12, 13, 14, 15, 16, 17, 18, 19, or 20); and wherein each R, independently, is a hydrogen atom or a $C_1$ to a $C_{30}$ (alternately $C_2$ to a $C_{30}$) branched or unbranched alkyl group.

3. The composition of paragraph 2, wherein each R alkyl group is ethyl, propyl, butyl, or isobutyl.

4. The composition of either of paragraphs 2 or 3, wherein x is 1, $R^1$ is propyl or pentyl, $R^2$ is a hydrogen atom and n is 1 or 2.

5. The composition of any of paragraphs 2 through 4, wherein the reaction product comprises a formula of, preferably is represented by the formula:

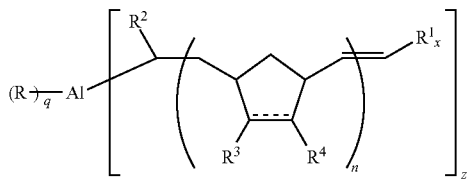

wherein $R^1$, $R^2$, $R^3$, $R^4$, each R if present, x, n, the dotted line and cis/trans relationships are as described above, and wherein z+q=3, preferably, z is 1, 2 or 3 and q is 0, 1 or 2.

6. The composition of paragraph 5, wherein z is 3 and q is 0.
7. The composition of paragraph 5, wherein z is 2 and q is 1.
8. The composition of paragraph 5, wherein z is 1 and q is 2.
9. A composition comprising the formula:

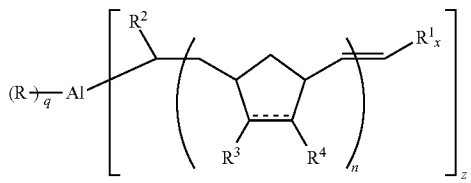

wherein the dotted line indicates an optional double bond; x is 0 or 1;

the double bonds depicted as trans can each, independently, be cis or trans;

$R^1$ and $R^2$ can be the same or different and each is a hydrogen atom or hydrocarbyl group having from one to twenty carbon atoms (preferably $R^2$ is a C5 or C6 hydrocarbyl);

$R^3$ and $R^4$ can be the same or different and each is a hydrogen atom or a hydrocarbyl group having from one to forty carbon atoms or $R^3$ and $R^4$ may be joined together to form a five-membered or six-membered ring, the ring having one or two optional double bonds;

n is an integer from 1 to 100 (alternately n is 1, 2, 3, 4, 5, 6, 7, 8, 9, 10, 11, 12, 13, 14, 15, 16, 17, 18, 19, or 20); and wherein each R, independently, is a hydrogen atom or a $C_1$ to a $C_{30}$ (alternately $C_2$ to a $C_{20}$) branched or unbranched alkyl group and z+q=3.

10. The composition of paragraph 9, wherein x is 1, $R^1$ is propyl or pentyl, $R^2$ is a hydrogen atom and n is 1 or 2.

11. The composition of either of paragraphs 9 or 10, wherein z is 3 and q is 0.

12. The composition of either of paragraphs 9 or 10, wherein z is 2 and q is 1.

13. The composition of either of paragraphs 9 or 10, wherein z is 1 and q is 2.

14. A catalyst system comprising:
a metallocene catalyst; and
the composition according to any of paragraphs 1 through 13.

15. A supported activator comprising an ion-exchange layered silicate and a composition of any of paragraphs 1 through 13.

16. The supported activator of paragraph 15, further comprising a metallocene catalyst.

17. A method to prepare a polymer, comprising the steps: contacting an olefin with any of the catalyst systems of paragraph 14 or the supported activator of paragraph 16 or 20.

18. The method of paragraph 17, wherein the olefin is propylene.

19. The method of claim 17 wherein the polymer produced is a propylene polymer.

20. A supported activator comprising an ion-exchange layered silicate and a composition of any of paragraphs 1 through 16, wherein the ion-exchange layered silicate is selected from the group consisting of montmorillonite, nontronite, beidellite, volkonskoite, laponite, hectorite, saponite, sauconite, stevensite (stephensite), vermiculite, halloysite, aluminate oxides, bentonite, kaolinite, dickite, smectic clays, mica, magadiite, kenyaite, octosilicate, kanemite, makatite, attapulgite, sepiolite, zeolitic layered materials, nacrite, metahalloysite, chrysotile, lizardite, antigorite, nontronite, illite, sericite, glauconite, attapulgite, palygorskite, pyrophyllite, talc, chlorites, preferably the ion-exchange layered silicate comprises montmorillonite.

Alternately this invention relates to:

1A. A composition comprising the reaction product of $AlH_3$ or a trialkyl aluminum and a cyclic vinyl terminated olefin.

2A. A composition comprising the reaction product of $Al(R)_3$ and a compound represented by the formula (I):

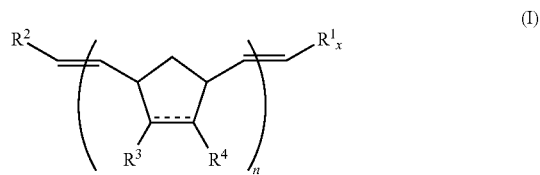

wherein the dotted line indicates an optional double bond; x is 0 or 1;

the double bonds depicted as trans can each, independently, be cis or trans; $R^1$ and $R^2$ can be the same or different and each is a hydrogen atom or hydrocarbyl group having from one to twenty carbon atoms; $R^3$ and $R^4$ can be the same or different and each is a hydrogen atom or a hydrocarbyl group having from one to forty carbon atoms or $R^3$ and $R^4$ may be joined together to form a five-membered or six-membered ring, the ring having one or two optional double bonds, provided that at least one of $R^1$ or $R^2$ is a hydrogen atom such that a vinyl end group is present; n is an integer from 1 to 100 (alternately n is 1, 2, 3, 4, 5, 6, 7, 8, 9, 10, 11, 12, 13, 14, 15, 16, 17, 18, 19, or 20); and wherein each R, independently, is a hydrogen atom or a $C_1$ to a $C_{30}$ (alternately $C_2$ to a $C_{20}$) branched or unbranched alkyl group.

3A. The composition of paragraph 2A, wherein each R alkyl group is selected from the group consisting of ethyl, propyl, butyl, isobutyl, or isomers thereof.

4A. The composition of either of paragraphs 2A or 3A, wherein x is 1, $R^1$ is propyl or pentyl, $R^2$ is a hydrogen atom and n is 1A or 2A.

5A. The composition of any of paragraphs 2A through 4A, wherein the reaction product comprises a formula of:

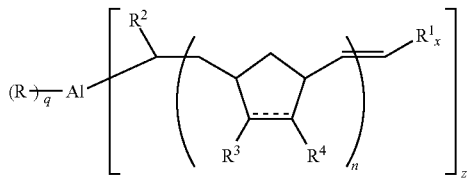

wherein z+q=3; wherein the dotted line indicates an optional double bond; x is 0 or 1; the double bonds depicted as trans can each, independently, be cis or trans; $R^1$ and $R^2$ can be the same or different and each is a hydrogen atom or hydrocarbyl group having from one to twenty carbon atoms; $R^3$ and $R^4$ can be the same or different and each is a hydrogen atom or a hydrocarbyl group having from one to forty carbon atoms or $R^3$ and $R^4$ may be joined together to form a five-membered or six-membered ring, the ring having one or two optional double bonds, provided that at least one of $R^1$ or $R^2$ is a hydrogen atom such that a vinyl end group is present; n is an integer from 1 to 100 (alternately n is 1, 2, 3, 4, 5, 6, 7, 8, 9, 10, 11, 12, 13, 14, 15, 16, 17, 18, 19, or 20); and wherein each R, independently, is a hydrogen atom or a $C_1$ to a $C_{30}$ (alternately $C_1$ to $C_{20}$) branched or unbranched alkyl group.

6A. The composition of paragraph 5A, wherein z is 3 and q is 0.

7A. The composition of paragraph 5A, wherein z is 2 and q is 1.

8A. The composition of paragraph 5A, wherein z is 1 and q is 2.

9A. A composition represented by the formula:

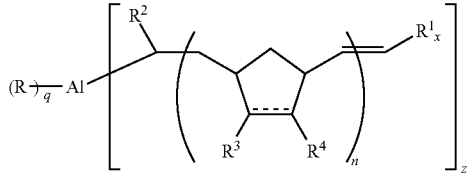

wherein the dotted line indicates an optional double bond; x is 0 or 1; the double bonds depicted as trans can each, independently, be cis or trans; $R^1$ and $R^2$ can be the same or different and each is a hydrogen atom or hydrocarbyl group having from one to twenty carbon atoms; $R^3$ and $R^4$ can be the same or different and each is a hydrogen atom or a hydrocarbyl group having from one to forty carbon atoms or $R^3$ and $R^4$ may be joined together to form a five-membered or six-membered ring, the ring having one or two optional double bonds; n is an integer from 1 to 100 (alternately n is 1, 2, 3, 4, 5, 6, 7, 8, 9, 10, 11, 12, 13, 14, 15, 16, 17, 18, 19, or 20); wherein each R, independently, is a hydrogen atom or a $C_1$ to a $C_{30}$ (alternately $C_2$ to $C_{20}$) branched or unbranched alkyl group; and z+q=3.

10A. The composition of paragraph 9A, wherein x is 1, $R^1$ is propyl or pentyl, $R^2$ is a hydrogen atom and n is 1 or 2.

11A. The composition of either of paragraphs 9A or 10A, wherein z is 3 and q is 0.

12A. The composition of either of paragraphs 9A or 10A, wherein z is 2 and q is 1.

13A. The composition of either of paragraphs 9A or 10A, wherein z is 1 and q is 2.

14A. A catalyst system comprising: a metallocene catalyst; and the composition according to any of paragraphs 1A through 13A or paragraph 24A.

15A. A supported activator comprising an ion-exchange layered silicate and a composition of any of paragraphs 1A through 13A.

16A. A supported activator comprising an ion-exchange layered silicate and a composition of any of paragraphs 1A through 13A, wherein the ion-exchange layered silicate is selected from the group consisting of montmorillonite, nontronite, beidellite, volkonskoite, laponite, hectorite, saponite, sauconite, stevensite, vermiculite, halloysite, aluminate oxides, bentonite, kaolinite, dickite, smectic clays, mica, magadiite, kenyaite, octosilicate, kanemite, makatite, attapulgite, sepiolite, zeolitic layered materials and mixtures thereof.

17A. A supported activator comprising an ion-exchange layered silicate and a composition of any of paragraphs 1A through 13A, wherein the ion-exchange layered silicate is selected from the group consisting of dickite, nacrite, kaolinite, metahalloysite, halloysite, chrysotile, lizardite, antigorite, montmorillonite, beidellite, nontronite, saponite, hectorite, stephensite, vermiculite, mica, illite, sericite, glauconite, attapulgite, sepiolite, palygorskite, bentonite, pyrophyllite, talc, chlorites.

18A. A supported activator comprising an ion-exchange layered silicate and a composition of any of paragraphs 1A through 13A, wherein the ion-exchange layered silicate comprises montmorillonite.

19A. The supported activator of paragraph 15A, 16A, 17A or 18A, further comprising a metallocene catalyst.

20A. A method to prepare a polymer, comprising the steps: contacting an olefin with any of the catalyst systems of paragraph 14A or the supported activator of paragraph 15A, 16A, 17A, 18A or 19A.

21A. The method of paragraph 20, wherein the olefin comprises one or more of ethylene, propylene, butene-1, pentene-1, 4-methyl-pentene-1, hexene-1, octene-1 and decene-1.

22A. The method of paragraph 20A, wherein the olefin is propylene and or ethylene.

23A. The method of paragraph 22A, wherein polymer produced is a propylene polymer and/or an ethylene polymer.

24A. The composition of paragraph 2A, wherein $R^2$ is a hydrocarbyl group having 5 or 6 carbon atoms.

25A. The method of paragraph 14A or the activator of paragraph 19A, wherein the metallocene catalyst comprises one or more of dimethylsilyl bis-(2-methyl-4-phenylindenyl)zirconium dichloride, dimethylsilyl bis(indenyl) hafnium dimethyl; dimethylsilanediyl-(2-methyl-4-(4'-tert-butylphenyl)indenyl(2-isopropyl-4-(4'-tert-butylphenyl)indenyl)zirconium dichloride, bis(1,3-methyl,n-butyl-cyclopentadienyl)zirconium dichloride, bis(1,3-methyl,n-butyl-cyclopentadienyl)zirconium dimethyl, dimethylsilylbis(2-methyl-indenyl)zirconium dichloride, dimethylsilyl bis(2-methyl-indenyl)zirconium dimethyl, dimethylsilyl bis(2-methyl,4,6-dipropyl-indenyl)zirconium dichloride; dimethylsilyl bis(2-methyl,4,6-dipropyl-indenyl)zirconium dimethyl; dimethylsilyl bis(2- methyl,4-phenyl-indenyl)zirconium dimethyl; dimethylsilyl bis(2-methyl,4-naphthyl-indenyl)zirconium dichloride; dimethylsilyl bis(2-methyl,4-naphthyl-indenyl)zirconium dimethyl; dimethylsilyl bis(2-ethyl,4-phenyl-indenyl)zirconium dichloride; dimethylsilyl bis(2-ethyl,4-phenyl-indenyl)zirconium dimethyl; dimethylsilyl bis(2-methyl,4-(di-tert-butyl-phenyl)-indenyl)zirconium dichloride; dimethylsilyl bis(2-methyl,4-(di-tert-butyl-phenyl)-indenyl)zirconium dimethyl, dimethylsilyl bis(2-methyl-indenyl)hafnium dichloride, dimethylsilyl bis(2-methyl-indenyl)hafnium dimethyl, dimethylsilyl bis(2-methyl,4,6-dipropyl-indenyl)hafnium dichloride; dimethylsilyl bis(2-methyl,4,6-dipropyl-indenyl)hafnium dimethyl; dimethylsilyl bis(2-methyl,4-phenyl-indenyl) hafnium dichloride; dimethylsilyl bis(2-methyl,4-phenyl-indenyl)hafnium dimethyl; dimethylsilyl bis(2-methyl,4-naphthyl-indenyl)hafnium dichloride; dimethylsilyl bis(2-methyl,4-naphthyl-indenyl)hafnium dimethyl; dimethylsilyl bis(2-ethyl,4-phenyl-indenyl)hafnium dichloride; dimethylsilyl bis(2-ethyl,4-phenyl-indenyl) hafnium dimethyl; dimethylsilyl bis(2-methyl,4-(di-tert-butyl-phenyl)-indenyl)hafnium dichloride; and dimethylsilyl bis(2-methyl,4-(di-tert-butyl-phenyl)-indenyl) hafnium dimethyl.

26A. The method of paragraph 14A or the activator of paragraph 19A, wherein the metallocene catalyst comprises one or more of $Me_2Si(ind)_2MX_2$, $Me_2Si(ind)_2MX_2$, $Me_2Si(2\text{-}Me\text{-}4\text{-}Ph\text{-}Ind)_2MX_2$, $Me_2Si(2\text{-}Me\text{-}benzindenyl)_2MX_2$, $Me_2Si(2\text{-}Me\text{-}Ind)_2MX_2$, $Me_2Si(2\text{-}Me\text{-}Ind)_2MX_2$, $Me_2Si(2\text{-}Me\text{-}4\text{-}naphthyl\text{-}indenyl)_2MX_2$, ethylene-bis$(Ind)_2MX_2$, $Me_2Si(2\text{-}Me\text{-}4\text{-}(2'\text{-}Me\text{-}Ph)\text{-}Ind)_2MX_2$, $Me_2Si(2\text{-}Me\text{-}4\text{-}(4'\text{-}Me\text{-}Ph)\text{-}Ind)_2MX_2$, $Me_2Si(2\text{-}methyl\text{-}4\text{-}(4'\text{-}t\text{-}Bu\text{-}Ph)\text{-}Ind)_2MX_2$, $Me_2Si(2\text{-}Me\text{-}4\text{-}(4'\text{-}t\text{-}Bu\text{-}Ph)\text{-}Ind)2\text{-}iPr\text{-}4\text{-}(4'\text{-}t\text{-}Bu\text{-}Ph\text{-}Ind)_2MX_2$, $Me_2Si(2\text{-}Me\text{-}4,6\text{-}iPr_2\text{-}Ind)_2MX_2$, $(Cp)_2MX_2$, $(Me_5Cp)_2MX_2$, $(Cp)(Me_5Cp)_2MX_2$, $(1\text{-}Me,4\text{-}Bu\text{-}Cp)_2MX_2$, $(1\text{-}Me,4\text{-}EtCp)_2MX_2$, $(1\text{-}Me,4\text{-}BzCp)_2MX_2$, $(1\text{-}Me,3\text{-}n\text{-}PrCp)_2MX_2$, $(1\text{-}Me,3\text{-}iPrCp)_2MX_2$, $(1,3\text{-}Me_2Cp)_2MX_2$, $(n\text{-}PrCp)_2MX_2$, $(n\text{-}BuCp)_2MX_2$, $(_{t\text{-}BuCp})_2MX_2$, $(BzCp)_2MX_2$, $(BzCp)(Me_5Cp)_2MX_2$, $(BzCp)(Me_5Cp)_2MX_2$, $(PrCp)(Me_5Cp)_2MX_2$, $(PrCp)(Me_4Cp)_2MX_2$, $(PrCp)(Me_4Cp)_2MX_2$, $(Me_4,PrCp)(Me_5Cp)_2MX_2$, $(Me_4,PrCp)(Cp)_2MX_2$, $Me_2Si(Cp)_2MX_2$, $Me_2Si(Cp)(Me_5Cp)_2MX_2$, $Me_2Si(1\text{-}Me,4\text{-}butylCp)_2MX_2$, $Me_2Si(1\text{-}Me,4\text{-}EtCp)_2MX_2$, $Me_2Si(1\text{-}Me,4\text{-}BzCp)_2MX_2$, $Me_2Si(1\text{-}Me,3\text{-}butylCp)_2MX_2$, $Me_2Si(1\text{-}Me,3\text{-}n\text{-}PrCp)_2MX_2$, $Me_2Si(1\text{-}Me,3\text{-}i\text{-}PrCp)_2MX_2$, $Me_2Si(1,3\text{-}Me_2Cp)_2MX_2$, $Me_2Si(n\text{-}PrCp)_2MX_2$, $Me_2Si(n\text{-}BuCp)_2MX_2$, $Me_2Si(t\text{-}Bu)(Cp)_2MX_2$, $Me_2Si(BzCp)_2MX_2$, $Me_2Si(BzCp)(Me_5Cp)_2MX_2$, $Me_2Si(PrCp)(Me_4Cp)_2MX_2$, $Me_2Si(Me_4,PrCp)(Me_5Cp)_2MX_2$, $Me_2Si(Me_4,PrCp)(Cp)_2MX_2$, and $Me_2Si(Me_4,PrCp)(Cp)_2MX_2$, where M is Hf or Zr and X is Cl, Me, —OMe, Bz, F, or amide.

27A. The method or activator of paragraph 26A, wherein M is Zr or Hf and X is Me or Cl.

EXAMPLES $^1$H NMR data was collected at 23° C. in a 5 mm probe using a 400 MHz Bruker spectrometer with deuterated tetrachloroethane. Data was recorded using a maximum pulse width of 45°, 8 seconds between pulses and signal averaging either 8 or 16 transients. The spectrum were normalized to protonated tetrachloroethane in the deuterated tetrachloroethane, which is expected to show a peak at 6.0 ppm.

The catalyst, $(HP(tBu)_2)_2Ru(C_5H_8)Cl_2$, was synthesized as described in US 2012/0309998 A1, Dec. 6, 2012. The olefin described as ROCM-(DCPD, 1-pentene) was obtained by the ring opening cross metathesis of 1-pentene and dicyclopentadiene, (145° C.@60 mTorr) as described in U.S. Ser. No. 13/209,242 Apr. 26, 2013.

ROCM is defined to mean ring opening cross metathesis. ROCM-(olefin A, olefin B) is a Polymer produced by the ROCM of olefin A and olefin B.

Synthesis of ROCM-(norbornene, 1-hexene):

1-hexene(15.0 g, 178 mmol, 1.30 eq) and the ROCM catalyst $[(HP(tBu)_2)_2Ru(C_5H_8)Cl_2]$ (6.0 mg, 0.011 mmol, 0.0008 eq) were added together in a 100 mL round bottom flask and heated to 40° C. Norbornene (12.9 g 94.1 mmol, 1 eq) was dissolved in approximately 5 mL of toluene and added dropwise to the stirring solution in a heating block set at room temperature. The thermocouple connected to the heating block and the flask indicated an exothermic reaction; at 50° C. the round bottom was placed in the freezer (−35° C.) for 1 hour to cool down. After further stirring for 1 hr at 40° C., then overnight (16 hrs) at room temperature; the reaction was taken out of the box and distilled. The distillation was checked periodically via $^1$H NMR in order to confirm removal of excess 1-hexene and toluene. The product was distilled with a short path distillation apparatus, then placed on a rotavap in order to remove excess toluene. $^1$H NMR analysis was a mixture of approximately 1 norbornene unit (21%) and 2 norbornene units (79%). 7.47 grams of product were collected.

Synthesis of Al-ROCM(DCPD, 1-pentene)$_3$

A 10.0 gram amount of ROCM-(DCPD, 1-pentene) was combined with 3.2 grams of tri-isobutylaluminum. The solution temperature was slowly raised from room temperature (over the course of one hour) to 145° C. After six hours at 145° C. bubbling had stopped. Cooling to room temperature yielded a viscous product. The reaction was followed by $^1$H NMR noting the disappearance of the vinyl resonances (multiplets at 5.8 and 5.0). $^1$H NMR (400 MHz, $CD_2ClCD_2Cl$), δ 5.7 (m), 5.5 (m) 3.3-0.5 (overlapping multiplets and singlets).

Synthesis of Al(ROCM-(norbornene, 1-hexene))x(isobutyl)y x+y=3

In a large thick-walled flask triisobutyl aluminum (1.048 g, 5.284 mmol) was weighed out. ROCM-(norbornene, 1-hexene) 1.34 g, was added neat. The flask was sealed and heated up to 210° C. for 2 hr. The flask was cooled to room temperature. $^1$H NMR analysis showed consumption of the vinyl end groups and new Al—$CH_2$ peaks. 0.894 g of green gel was collected.

Synthesis of Clay Treated Cyclic Alkyl Aluminum Supports for Single Site Catalyst Activation Acid treated clay was prepared by placing 101 grams of Montmorillonite KSF™ (20-40 m$^2$/g surface area, obtained from Sigma Aldrich), in a 500 mL round bottom flask along with 377 mL of $H_2O$ and 55 mL of concentrated sulfuric acid then stirring for 6 hr 43 min at 90° C. The mixture was allowed to stir overnight at room temperature. The mixture was then filtered and the solid was washed with 5×150 mL of $H_2O$. The pH of the filtrate was monitored, when the pH was approximately 3 the washing was stopped and the solid was placed under vacuum at room temperature overnight. The product was then placed under nitrogen purge at 130° C. over the weekend. The product was brought into a glovebox while maintaining a nitrogen atmosphere. 58.8 g of product acid treated Montmorillonite KSF™ was collected.

Supported Catalyst 1: rac-$Me_2Si$(2-methyl-4-phenyl-1-indenyl)$_2ZrMe_2$/Clay-Al-(ROCM-(norbornene,1-hexene))x (isobutyl)y x+y=2

Acid treated montmorillonite KSF™ (0.905 g) was slurried in 30 mL of toluene and sonicated for 3 min before 0.894 g of compound Al(ROCM-(norbornene,1-hexene))x(isobutyl)y x+y=3 was added to the mixture. The mixture was sonicated for 30 min. $^1$H NMR analysis showed excess Al containing species. The solid was washed twice with 20 mL of toluene and reslurried in 25 mL of toluene. Product of acid treated montmorillonite KSF™/Al(ROCM-(norbornene,1-hexene))x(isobutyl)y was obtained (referred to as Clay A). Separately, rac-Me$_2$Si(2-methyl-4-phenyl-1-indenyl)$_2$ZrMe$_2$ (21 mg, 0.036mmol) was dissolved in 10 mL of toluene, then combined with Clay A and sonicated for 30 min. The solid was filtered and washed three times with toluene and once with pentane. The gray brown solid was dried under vacuum for 1.5 hr. 0.917 g of gray/brown powder was collected.

Supported Catalyst 2: rac-Me$_2$Si(2-methyl-4-phenyl-1-indenyl)$_2$ZrMe$_2$/clay-Al-(ROCM-(DCPD, 1-pentene))$_2$ In a 250 mL round bottom flask 0.335 g of Al-ROCM (DCPD, 1-pentene)$_3$ was dissolved in 45 mL of toluene then placed in an oil bath at 60° C. Acid treated Montmorillonite KSF™ (1.00 g) was added as a solid and stirred for 1 hr at 100° C. A $^1$H NMR was taken and showed that most, if not all, of the Al-ROCM(DCPD, 1-pentene)$_3$ was consumed. An additional 0.230 g of Al-ROCM(DCPD, 1-pentene)$_3$ was added to the mixture and stirred 30 min. A second $^1$H NMR shows excess cyclic alkyl aluminum. The solid of Acid treated Montmorillonite KSF™/Al-ROCM(DCPD, 1-pentene)$_3$ was filtered, washed with 2×25 mL of toluene, and then reslurried in 35 mL of toluene in a 100 mL round bottom flask. Separately, rac-Me$_2$Si(2-methyl-4-phenyl-1-indenyl)$_2$ZrMe$_2$ (22.0 mg, 0.0374 mmol) was dissolved in 15 mL of toluene and then added to the slurry. The slurry was stirred overnight at room temperature. The resulting product was then filtered and washed with 4×25 mL of toluene. The solid obtained was dried under vacuum. 1.03 g of a pink/purple solid was collected.

Bench Scale Polymerizations with Propylene

Polymerization Example 1

A catalyst tube was loaded with a tri-n-octylaluminum (TNOAL) solution (3 mL of 0.091M solution in hexane) and injected into the reactor (two liter autoclave) with nitrogen. The 35 mL catalyst tube was then pressurized up with 42 psi of hydrogen which was then added to the reactor. 600 mL of propylene was added to the reactor through the catalyst tube. The reactor was heated up to 70° C. with a stir rate set at 500 rpm. Supported catalyst 2 (27.4 mg) was loaded into a second catalyst tube along with 3 mL of hexane and was inserted into the reactor via 200 mL of propylene. The reactor was run for 1 hour at 70° C. 17.44 g of white solid was collected. Activity: 636.5 g polymer/(g cat*hr). 1700 g polymer/(mmol Zr*hr).

Polymerization Example 2

A 25 mL cat tube was loaded with 2 mL of a 0.091M TNOAL solution which was then injected into the reactor. The cat tube was pressurized with 28 psi of hydrogen which was then injected into the reactor alongside 350 mL of propylene. The reactor was heated to 70° C. with the stir rate set to 500 rpm. A second catalyst tube containing supported catalyst 1 (70.1mg) was attached to the reactor. The catalyst was pushed into the reactor with 150 mL of propylene. The reaction was set to stir for 1 hour at 70° C. The reactor was vented and 20.7 g of fine white powder was collected. Activity: 294 g polymer/(g cat*hr).

Small Scale Polymerization Procedures
1. Propylene Polymerizations
General Procedure for Small Scale Solution Polymerization Unless stated otherwise, ethylene homopolymerizations were carried out in a parallel, pressure reactor, as generally described in U.S. Pat. Nos. 6,306,658; 6,455,316; 6,489,168; WO 00/09255; and Murphy et al., J. Am. Chem. Soc., 2003, 125, pp. 4306-4317, each of which is fully incorporated herein by reference for US purposes to the extent not inconsistent with this disclosure. Although the specific quantities, temperatures, solvents, reactants, reactant ratios, pressures, and other variables are frequently changed from one polymerization run to the next, the following describes a typical polymerization performed in a parallel, pressure reactor.

A pre-weighed glass vial insert and disposable stirring paddle were fitted to each reaction vessel of the reactor, which contains 48 individual reaction vessels. The reactor was then closed, then ethylene (135 psi (931 kPa)) was added to each vessel. Then solvent (typically isohexane) was added to bring the total reaction volume, including the subsequent additions, to 5 mL and the reactor vessels were heated to their set temperature (70° C. and 90° C.) (see table). At this time scavenger and/or co-catalyst, such as tri-n-octylaluminum or Al-ROCM(DCPD, 1-pentene)$_3$ in toluene (approximately 1 micromole) was added.

The contents of the vessel were stirred at 800 rpm. An activator solution (typically 1.0-1.2 molar equivalents of dimethyl anilinium tetrakis-pentafluorophenyl) was then injected into the reaction vessel along with 500 microliters of toluene, followed by a toluene solution of catalyst compound (typically 0.40 mM in toluene, usually 20-40 nanomols of catalyst) and another aliquot of toluene (500 microliters). Equivalence is determined based on the mol equivalents relative to the moles of the transition metal in the catalyst complex.

The reaction was then allowed to proceed until a predetermined amount of pressure had been taken up by the reaction. Alternatively, the reaction may be allowed to proceed for a set amount of time. At this point, the reaction was quenched by pressurizing the vessel with compressed air. After the polymerization reaction, the glass vial insert containing the polymer product and solvent was removed from the pressure cell and the inert atmosphere glove box, and the volatile components were removed using a Genevac HT-12 centrifuge and Genevac VC3000D vacuum evaporator operating at elevated temperature and reduced pressure. The vial was then weighed to determine the yield of the polymer product. The resultant polymer was analyzed by Rapid GPC (see below) to determine the molecular weight.

To determine various molecular weight related values by GPC, high temperature size exclusion chromatography was performed using an automated "Rapid GPC" system as generally described in U.S. Pat. Nos. 6,491,816; 6,491,823; 6,475,391; 6,461,515; 6,436,292; 6,406,632; 6,175,409; 6,454,947; 6,260,407; and 6,294,388; each of which is fully incorporated herein by reference for US purposes. This apparatus has a series of three 30 cm×7.5 mm linear columns, each containing PLgel 10 um, Mix B. The GPC system was calibrated using polystyrene standards ranging from 580-3,390,000 g/mol. The system was operated at an eluent flow rate of 2.0 mL/minutes and an oven temperature of 165° C. 1,2,4-trichlorobenzene was used as the eluent. The polymer samples were dissolved in 1,2,4-trichlorobenzene at a concentration of 0.1-0.9 mg/mL. 250 uL of a polymer solution was injected into the system. The concentration of the polymer in the eluent was monitored using an evaporative light scattering detector. The molecular weights presented are relative to linear polystyrene standards and are uncorrected.

Catalyst 1 is (dimethylsilanediyl-(6-methyl-4-phenyl-1,2,3,5-tetrahydro-s-indacen-7-yl)-2-isopropyl-4-(4'-tert-butylphenyl)-1-indenyl)-zirconium dichloride.

TNOAL is tri-n-octyl aluminum.

Alkyl Aluminum DCPD is AL-ROCM(DCPD, 1-pentene)$_3$.

Catalyst 2 is dimethylsilyl bis-(2-methyl-4-phenylindenyl) zirconium dichloride.

Catalyst 3 is dimethylsilyl bis(indenyl)hafnium dimethyl.

Catalyst 4 is (dimethylsilanediyl-(2-methyl-4-(4'-tert-butylphenyl)indenyl(2-isopropyl-4-(4'-tert-butylphenyl)indenyl)zirconium dichloride.

| Catalyst | Alkyl Aluminum | Activity (gP/mmolcat · hr) | Mn (g/mol) | Mw (g/mol) | Mw/Mn | Rxn Temp. (° C.) |
|---|---|---|---|---|---|---|
| 1 | TNOAl | 128.2 | 517203 | 1300764 | 2.51 | 70 |
| 1 | TNOAl | 119.2 | 705782 | 1459628 | 2.07 | 70 |
| 1 | TNOAl | 104.8 | 297166 | 636997 | 2.14 | 90 |
| 1 | Al-ROCM(DCPD, 1-pentene)$_3$ | 127.7 | 640964 | 1431349 | 2.23 | 70 |
| 1 | Al-ROCM(DCPD, 1-pentene)$_3$ | 95.4 | 1157837 | 1939793 | 1.68 | 70 |
| 1 | Al-ROCM(DCPD, 1-pentene)$_3$ | 133.6 | 563541 | 1349404 | 2.39 | 70 |
| 1 | Al-ROCM(DCPD, 1-pentene)$_3$ | 109.3 | 272337 | 624300 | 2.29 | 90 |
| 1 | Al-ROCM(DCPD, 1-pentene)$_3$ | 88.8 | 437001 | 783106 | 1.79 | 90 |
| 1 | Al-ROCM(DCPD, 1-pentene)$_3$ | 87.5 | 373597 | 699481 | 1.87 | 90 |
| 4 | TNOAl | 94.3 | 1056626 | 1854727 | 1.76 | 70 |
| 4 | TNOAl | 79.7 | 1504818 | 2356372 | 1.57 | 70 |
| 4 | TNOAl | 92.2 | 1068704 | 1869536 | 1.75 | 70 |
| 4 | TNOAl | 42.5 | 687287 | 1121947 | 1.63 | 90 |
| 4 | TNOAl | 51.8 | 700229 | 1150821 | 1.64 | 90 |
| 4 | TNOAl | 31.3 | 723355 | 1171866 | 1.62 | 90 |
| 4 | Al-ROCM(DCPD, 1-pentene)$_3$ | 106.1 | 967530 | 1783911 | 1.84 | 70 |
| 4 | Al-ROCM(DCPD, 1-pentene)$_3$ | 99.5 | 1153070 | 1978842 | 1.72 | 70 |
| 4 | Al-ROCM(DCPD, 1-pentene)$_3$ | 102.0 | 1039595 | 1781577 | 1.71 | 70 |
| 4 | Al-ROCM(DCPD, 1-pentene)$_3$ | 69.5 | 611834 | 1049183 | 1.71 | 90 |
| 4 | Al-ROCM(DCPD, 1-pentene)$_3$ | 66.2 | 611959 | 1036122 | 1.69 | 90 |
| 4 | Al-ROCM(DCPD, 1-pentene)$_3$ | 45.3 | 685748 | 1099447 | 1.60 | 90 |
| 2 | TNOAl | 149.2 | 234380 | 498847 | 2.13 | 70 |
| 2 | TNOAl | 156.3 | 269808 | 541145 | 2.01 | 70 |
| 2 | TNOAl | 148.6 | 278189 | 534335 | 1.92 | 70 |
| 2 | TNOAl | 59.7 | 461095 | 908475 | 1.97 | 90 |
| 2 | TNOAl | 107.9 | 181408 | 356987 | 1.97 | 90 |
| 2 | Al-ROCM(DCPD, 1-pentene)$_3$ | 157.2 | 227072 | 533025 | 2.35 | 70 |
| 2 | Al-ROCM(DCPD, 1-pentene)$_3$ | 156.5 | 229530 | 534663 | 2.33 | 70 |
| 2 | Al-ROCM(DCPD, 1-pentene)$_3$ | 146.9 | 249920 | 536865 | 2.15 | 70 |
| 2 | Al-ROCM(DCPD, 1-pentene)$_3$ | 109.5 | 178426 | 351704 | 1.97 | 90 |
| 2 | Al-ROCM(DCPD, 1-pentene)$_3$ | 111.9 | 185414 | 361714 | 1.95 | 90 |
| 2 | Al-ROCM(DCPD, 1-pentene)$_3$ | 107.7 | 174148 | 346476 | 1.99 | 90 |
| 3 | TNOAl | 115.4 | 267437 | 574888 | 2.15 | 70 |
| 3 | TNOAl | 113.6 | 268593 | 581894 | 2.17 | 70 |
| 3 | TNOAl | 87.4 | 396936 | 723137 | 1.82 | 70 |
| 3 | TNOAl | 71.6 | 231736 | 428667 | 1.85 | 90 |
| 3 | TNOAl | 77.8 | 229289 | 426704 | 1.86 | 90 |
| 3 | Al-ROCM(DCPD, 1-pentene)$_3$ | 135.3 | 149646 | 588237 | 3.93 | 70 |
| 3 | Al-ROCM(DCPD, 1-pentene)$_3$ | 132.3 | 175970 | 648617 | 3.69 | 70 |
| 3 | Al-ROCM(DCPD, 1-pentene)$_3$ | 142.1 | 315594 | 707708 | 2.24 | 70 |
| 3 | Al-ROCM(DCPD, 1-pentene)$_3$ | 105.8 | 114816 | 381969 | 3.33 | 90 |
| 3 | Al-ROCM(DCPD, 1-pentene)$_3$ | 73.2 | 329077 | 626068 | 1.90 | 90 |

Mw, Mn, Mw/Mn determined by Rapid GPC method.

All documents described herein are incorporated by reference herein for purposes of all jurisdictions where such practice is allowed, including any priority documents, related applications, and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law. Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

The invention claimed is:

1. A composition comprising the reaction product of $AlH_3$ or a trialkyl aluminum and a cyclic vinyl terminated olefin.

2. A composition comprising the reaction product of:
$Al(R)_3$ and a compound represented by the formula (I):

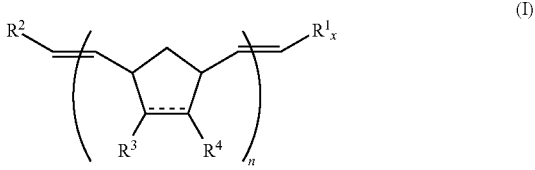

(I)

wherein the dotted line indicates an optional double bond;
x is 0 or 1;
the double bonds depicted as trans can each, independently, be cis or trans;
$R^1$ and $R^2$ can be the same or different and each is a hydrogen atom or hydrocarbyl group having from one to twenty carbon atoms;
each $R^3$ and $R^4$ can be the same or different and each is a hydrogen atom or a hydrocarbyl group having from one to forty carbon atoms or $R^3$ and $R^4$ may be joined together to form a five-membered or six-membered ring, the ring having one or two optional double bonds, provided that at least one of $R^1$ or $R^2$ is a hydrogen atom such that a vinyl end group is present;
n is an integer from 1 to 100; and
wherein each R, independently, is a hydrogen atom or a $C_1$ to a $C_{30}$ branched or unbranched alkyl group.

3. The composition of claim 2, wherein each R alkyl group is selected from the group consisting of ethyl, propyl, butyl, isobutyl, or isomers thereof.

4. The composition of claim 2 wherein x is 1, $R^1$ is propyl or pentyl, $R^2$ is a hydrogen atom and n is 1 or 2.

5. The composition of claim 2, wherein the reaction product comprises a formula of:

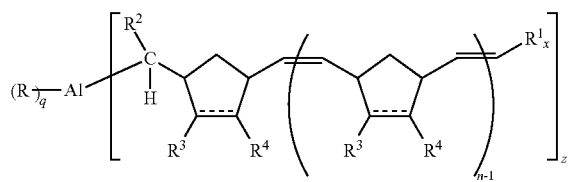

wherein z+q=3;
wherein the dotted line indicates an optional double bond;
x is 0 or 1;
the double bonds depicted as trans can each, independently, be cis or trans;
$R^1$ and $R^2$ can be the same or different and each is a hydrogen atom or hydrocarbyl group having from one to twenty carbon atoms;
each $R^3$ and $R^4$ can be the same or different and each is a hydrogen atom or a hydrocarbyl group having from one to forty carbon atoms or $R^3$ and $R^4$ may be joined together to form a five-membered or six-membered ring, the ring having one or two optional double bonds, provided that at least one of $R^1$ or $R^2$ is a hydrogen atom such that a vinyl end group is present;
n is an integer from 1 to 100; and
wherein each R, independently, is a hydrogen atom or a $C_1$ to a $C_{30}$ branched or unbranched alkyl group.

6. The composition of claim 5, wherein z is 3 and q is 0.
7. The composition of claim 5, wherein z is 2 and q is 1.
8. The composition of claim 5, wherein z is 1 and q is 2.
9. A composition represented by the formula:

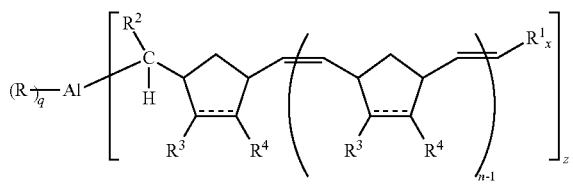

wherein the dotted line indicates an optional double bond;
x is 0 or 1;
the double bonds depicted as trans can each, independently, be cis or trans;
$R^1$ and $R^2$ can be the same or different and each is a hydrogen atom or hydrocarbyl group having from one to twenty carbon atoms;
each $R^3$ and $R^4$ can be the same or different and each is a hydrogen atom or a hydrocarbyl group having from one to forty carbon atoms or $R^3$ and $R^4$ may be joined together to form a five-membered or six-membered ring, the ring having one or two optional double bonds;
n is an integer from 1 to 100;
wherein each R, independently, is a hydrogen atom or a $C_1$ to a $C_{30}$ branched or unbranched alkyl group; and
z+q=3.

10. The composition of claim 9, wherein x is 1, $R^1$ is propyl or pentyl, $R^2$ is a hydrogen atom and n is 1 or 2.
11. The composition of claim 9, wherein z is 3 and q is 0.
12. The composition of claim 9, wherein z is 2 and q is 1.
13. The composition of claim 9, wherein z is 1 and q is 2.
14. The composition of claim 2, wherein $R^2$ is a hydrocarbyl group having 5 or 6 carbon atoms.
15. The composition of claim 2, wherein n is 1, 2, 3, 4, 5, 6, 7, 8, 9, 10, 11, 12, 13, 14, 15, 16, 17, 18, 19, or 20.
16. The composition of claim 2, wherein R is a $C_2$ to $C_{20}$ branched or unbranched alkyl group.

* * * * *